US012736602B2

(12) United States Patent
Ookawa

(10) Patent No.: US 12,736,602 B2
(45) Date of Patent: Sep. 15, 2026

(54) MRI APPARATUS

(71) Applicant: CANON KABUSHIKI KAISHA, Tokyo (JP)

(72) Inventor: Masashi Ookawa, Nasushiobara (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 96 days.

(21) Appl. No.: 18/811,873

(22) Filed: Aug. 22, 2024

(65) Prior Publication Data

US 2025/0067829 A1 Feb. 27, 2025

(30) Foreign Application Priority Data

Aug. 25, 2023 (JP) ................................ 2023-137290

(51) Int. Cl.

| | |
|---|---|
| ***G01R 33/56*** | (2006.01) |
| ***A61B 5/00*** | (2006.01) |
| ***A61B 5/055*** | (2006.01) |
| ***G01R 33/48*** | (2006.01) |
| ***G01R 33/565*** | (2006.01) |

(52) U.S. Cl.

CPC ........ *G01R 33/56518* (2013.01); *A61B 5/055* (2013.01); *A61B 5/7292* (2013.01); *G01R 33/4828* (2013.01)

(58) Field of Classification Search

CPC .......... G01R 33/56518; G01R 33/4828; A61B 5/055; A61B 5/7292

See application file for complete search history.

(56) References Cited

U.S. PATENT DOCUMENTS

2019/0018092 A1* 1/2019 Ookawa .............. G01R 33/561

FOREIGN PATENT DOCUMENTS

JP 2019-017494 A 2/2019

* cited by examiner

*Primary Examiner* — G.M. A Hyder

(74) *Attorney, Agent, or Firm* — Oblon, McClelland, Maier & Neustadt, L.L.P.

(57) ABSTRACT

In one embodiment, an MRI apparatus includes processing circuitry configured to continuously generate time-point data in increments of a predetermined time length; generate a series of gradient magnetic fields based on a predetermined pulse sequence; acquire an external trigger in association with trigger-time-point data corresponding to an acquisition time point of the external trigger; estimate a value of an eddy magnetic field at a second time point by using the gradient magnetic fields and respective time differences between the first time-point data and the second time-point data, wherein the respective time differences change depending on when the external trigger is acquired; calculate a frequency or phase variation of an MR signal at the second time point; and correct a frequency or phase of an RF transmitting signal or the MR signal, by using the calculated frequency variation or the phase variation.

11 Claims, 14 Drawing Sheets

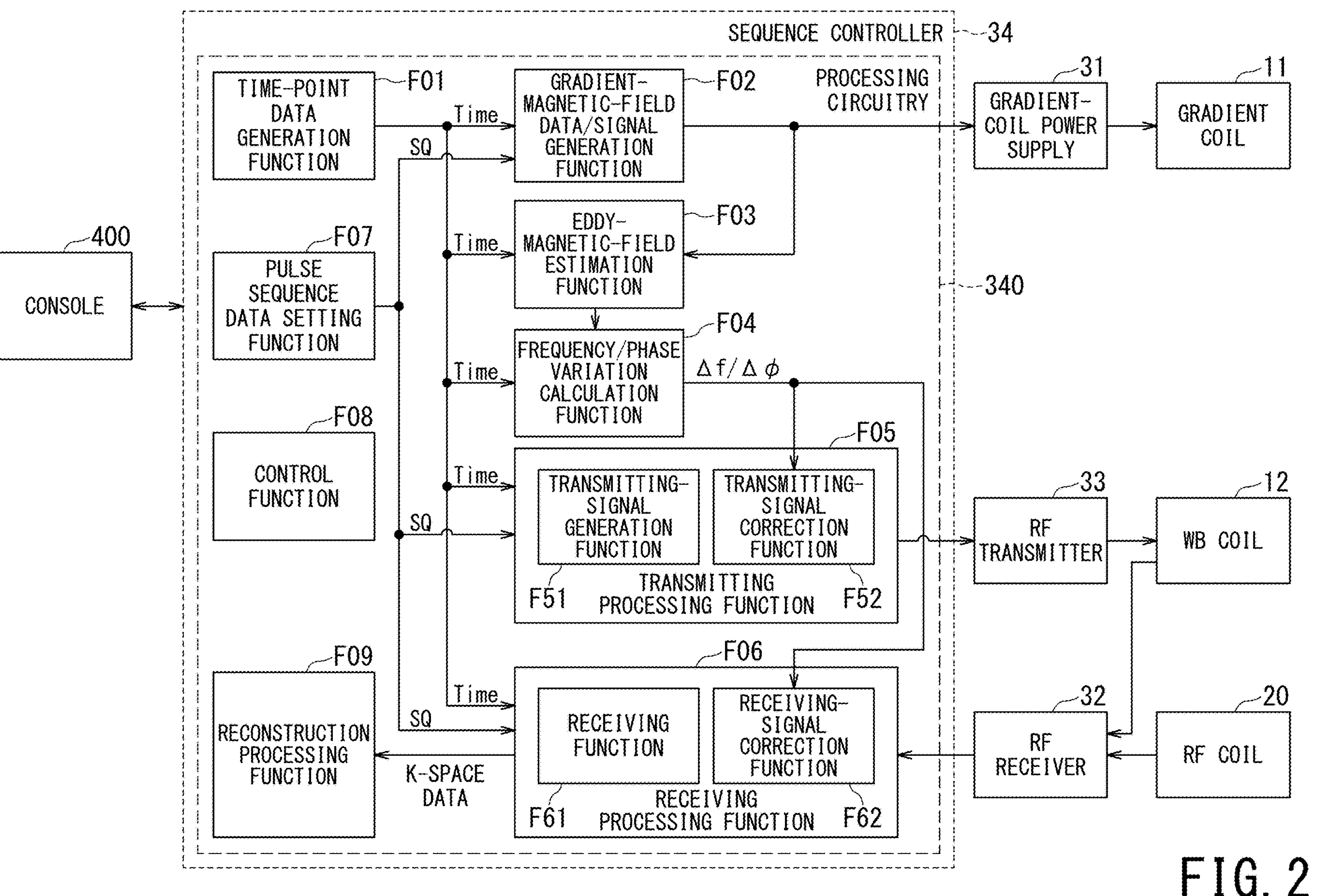
SEQUENCE CONTROLLER
34
PROCESSING CIRCUITRY
340
400
CONSOLE
F01
TIME-POINT DATA GENERATION FUNCTION
F07
PULSE SEQUENCE DATA SETTING FUNCTION
F08
CONTROL FUNCTION
F09
RECONSTRUCTION PROCESSING FUNCTION
F02
GRADIENT-MAGNETIC-FIELD DATA/SIGNAL GENERATION FUNCTION
F03
EDDY-MAGNETIC-FIELD ESTIMATION FUNCTION
F04
FREQUENCY/PHASE VARIATION CALCULATION FUNCTION
Δf/Δφ
F05
TRANSMITTING-SIGNAL GENERATION FUNCTION
TRANSMITTING-SIGNAL CORRECTION FUNCTION
F51
TRANSMITTING PROCESSING FUNCTION
F52
F06
RECEIVING FUNCTION
RECEIVING-SIGNAL CORRECTION FUNCTION
F61
RECEIVING PROCESSING FUNCTION
F62
Time
SQ
K-SPACE DATA
31
GRADIENT-COIL POWER SUPPLY
11
GRADIENT COIL
33
RF TRANSMITTER
12
WB COIL
32
RF RECEIVER
20
RF COIL
FIG. 2

FIG. 4A
TIME-
POINT DATA

FIG. 4B
RF PULSE
EXCITATION
PULSE
REFOCUSING
PULSE
EXCITATION
PULSE
REFOCUSING
PULSE

FIG. 4C
Gss

FIG. 4D
Gpe

FIG. 4E
Gro

FIG. 4F
MR SIGNAL

FIG. 5A
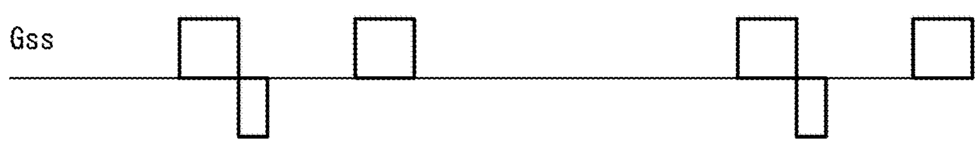
FIG. 5B
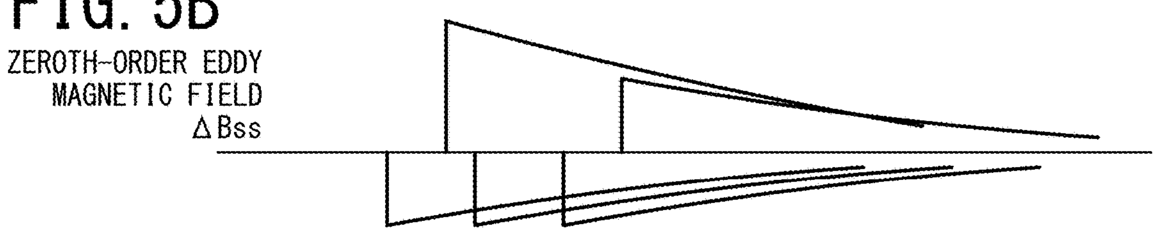
FIG. 5C
FIG. 5D
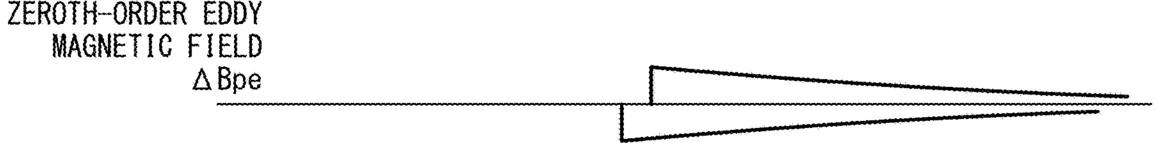
FIG. 5E
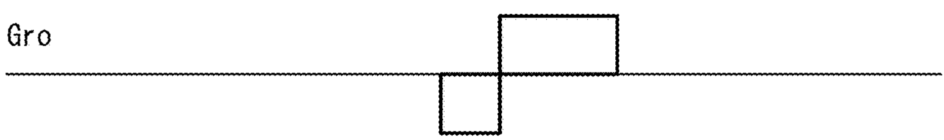
FIG. 5F
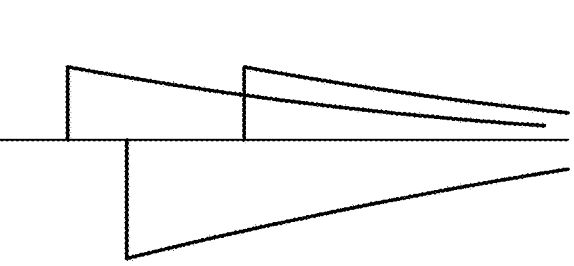
FIG. 5G
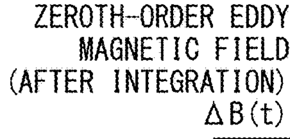
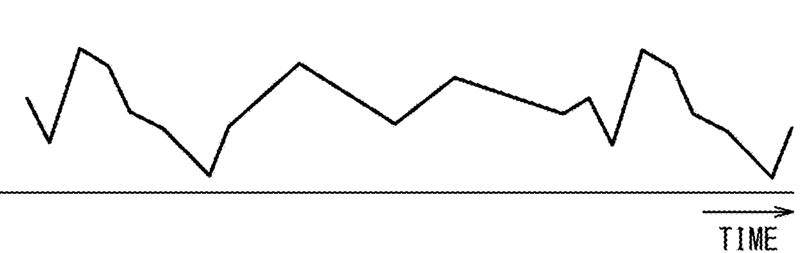

TIME-POINT DATA
A SERIES OF FIRST TIME-POINT DATA
SECOND TIME-POINT DATA
Tpast

Gss

Gpe
A SERIES OF FIRST TIME-POINT DATA

Gro
A SERIES OF GRADIENT MAGNETIC FIELDS
SECOND TIME-POINT DATA

ZEROTH-ORDER EDDY MAGNETIC FIELD (AFTER INTEGRATION) ΔB(t)
Δf/Δφ
REFOCUSING PULSE
EXCITATION PULSE

RF PULSE

TIME-POINT DATA
A SERIES OF FIRST TIME-POINT DATA
SECOND TIME-POINT DATA
Tpast

Gss

Gpe
A SERIES OF FIRST TIME-POINT DATA

Gro
A SERIES OF GRADIENT MAGNETIC FIELDS
SECOND TIME-POINT DATA

ZEROTH-ORDER EDDY MAGNETIC FIELD (AFTER INTEGRATION) ΔB(t)
Δf/Δφ

MR SIGNAL

FIG. 10A MR SIGNAL (ANALOG)
TIME
SAMPLING PERIOD
FIG. 10B MR SIGNAL (DIGITAL) (BEFORE CORRECTION)
S(t)
FIG. 10C PHASE VARIATION OF MR SIGNAL DUE TO EDDY MAGNETIC FIELD
Δφ(t)
FIG. 10D MR SIGNAL (DIGITAL) (AFTER CORRECTION)
S'(t)=S(t)·exp[−jΔφ(t)]

TIME-POINT DATA
A SERIES OF FIRST TIME-POINT DATA
SECOND TIME-POINT DATA
Tpast
Tdl

EXTERNAL TRIGGER

Gss

Gpe
A SERIES OF FIRST TIME-POINT DATA

Gro
A SERIES OF GRADIENT MAGNETIC FIELDS
SECOND TIME-POINT DATA

ZEROTH-ORDER EDDY MAGNETIC FIELD (AFTER INTEGRATION) ΔB(t)
REFOCUSING PULSE
EXCITATION PULSE
Δf/Δφ

RF PULSE

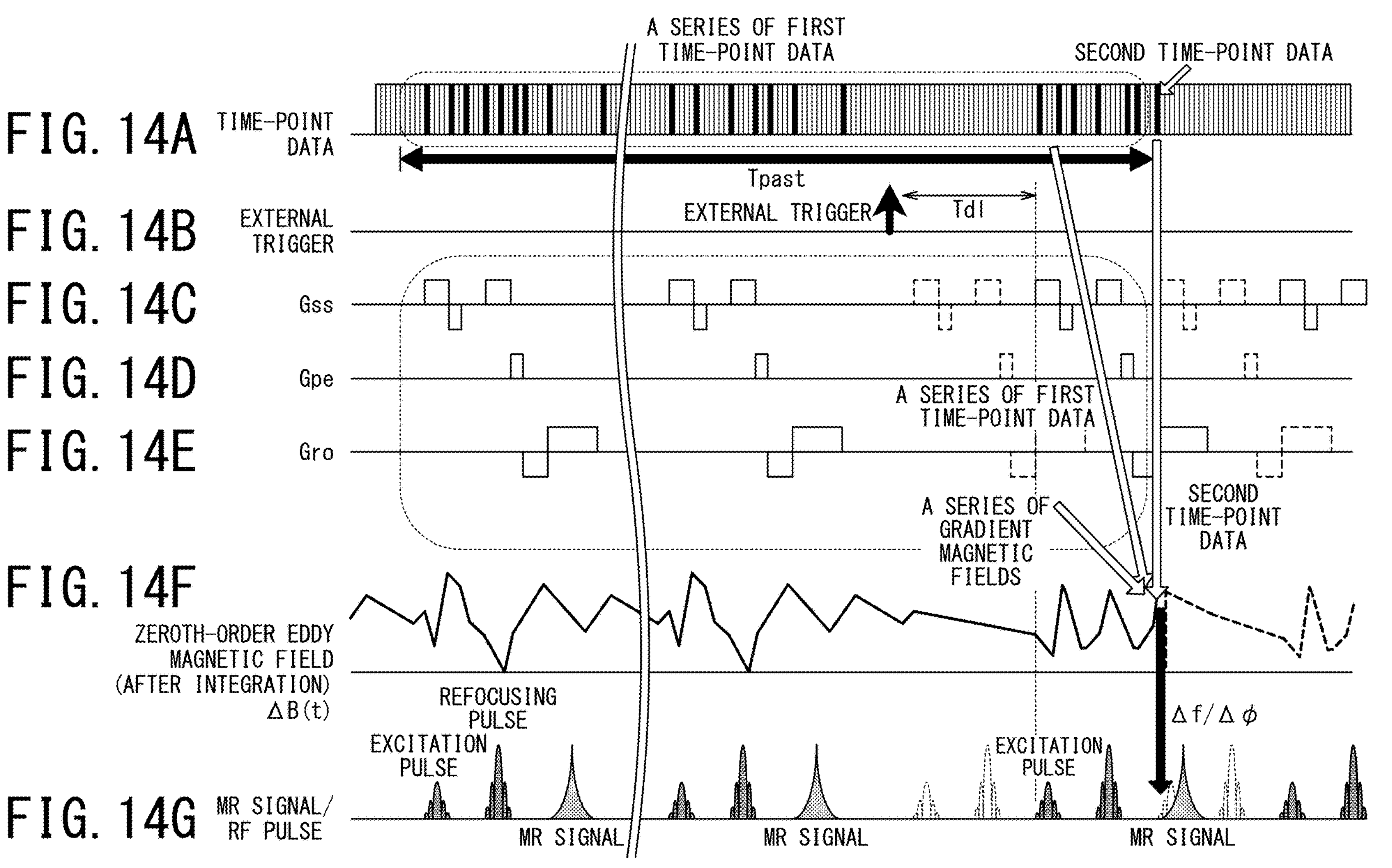
A SERIES OF FIRST TIME-POINT DATA
SECOND TIME-POINT DATA
FIG. 14A TIME-POINT DATA
Tpast
EXTERNAL TRIGGER
Tdl
FIG. 14B EXTERNAL TRIGGER
FIG. 14C Gss
FIG. 14D Gpe
A SERIES OF FIRST TIME-POINT DATA
FIG. 14E Gro
A SERIES OF GRADIENT MAGNETIC FIELDS
SECOND TIME-POINT DATA
FIG. 14F
ZEROTH-ORDER EDDY MAGNETIC FIELD (AFTER INTEGRATION) ΔB(t)
Δf/Δφ
REFOCUSING PULSE
EXCITATION PULSE
EXCITATION PULSE
FIG. 14G MR SIGNAL/ RF PULSE
MR SIGNAL
MR SIGNAL
MR SIGNAL

MRI APPARATUS

CROSS-REFERENCE TO RELATED APPLICATION

This application is based upon and claims the benefit of priority from Japanese Patent Application No. 2023-137290, filed on Aug. 25, 2023, the entire contents of which are incorporated herein by reference.

TECHNICAL FIELD

Disclosed embodiments relate to a magnetic resonance imaging (MRI) apparatus.

BACKGROUND

An MRI apparatus is an imaging apparatus that excites nuclear spin of an object placed in a static magnetic field by applying a radio frequency (RF) signal having the Larmor frequency and reconstructs an image on the basis of magnetic resonance (MR) signals emitted from the object due to the excitation.

Disturbance of the magnetic field caused by eddy currents is known as one of factors resulting in deterioration in image quality of magnetic resonance images. When a pulse current is applied to a gradient coil, because of the leakage magnetic field of the gradient magnetic field, an eddy current flows through metal, such as a heat shield plate of a static magnetic field coil, in the vicinity of the gradient coil. An eddy current magnetic field (hereinafter abbreviated as an "eddy magnetic field") is generated by each eddy current.

The static magnetic field or the gradient magnetic field is disturbed by the eddy magnetic fields, which cause deterioration in image quality. In particular, it is known that a variation of the zeroth-order component of the magnetic fields resulting from the eddy magnetic fields causes a variation of the magnetic resonance frequency.

Some methods have been proposed for suppressing the variation of zeroth-order component of the magnetic fields caused by the eddy current magnetic fields, i.e., eddy magnetic fields. For example, in a known method, a variation in magnetic resonance frequency at a certain time point is calculated by accumulating eddy magnetic fields resulting from a series of gradient magnetic fields applied in the past before this time point.

However, in the above-described conventional method, the cumulative value of the eddy magnetic fields cannot be accurately determined when imaging is performed in synchronization with an external trigger signal such as an ECG (electrocardiogram) signal, and the deterioration in image quality caused by the eddy magnetic fields cannot be sufficiently suppressed.

BRIEF DESCRIPTION OF THE DRAWINGS

In the accompanying drawings:

FIG. 2 is a block diagram illustrating a configuration and functions of a sequence controller;

FIG. 4A to FIG. 4F are timing charts illustrating a pulse sequence together with time-point data;

FIG. 5A to FIG. 5G are timing charts schematically illustrating temporal behavior of respective zeroth-order eddy magnetic fields generated by a series of gradient magnetic fields and behavior of a variation in the integrated eddy magnetic field obtained by integrating these zeroth-order eddy magnetic fields;

FIG. 14A to FIG. 14G are timing charts illustrating a concept of the receiving processing when the external trigger is inputted.

DETAILED DESCRIPTION

Hereinbelow, embodiments of the MRI apparatus will be described by referring to the accompanying drawings. In the following embodiments, components denoted by the same reference signs are the same in terms of configuration or function, and duplicate descriptions are omitted.

In one embodiment, an MRI apparatus includes processing circuitry configured to continuously generate time-point data in increments of a predetermined time length; generate a series of gradient magnetic fields based on a predetermined pulse sequence in association with a series of first time-point data that are the generated time-point data and correspond to respective generation time points of the series of gradient magnetic fields; acquire an external trigger in association with trigger-time-point data that are the generated time-point data and correspond to an acquisition time point of the external trigger; estimate a value of an eddy magnetic field at a second time point by using the series of gradient magnetic fields and respective time differences between the series of first time-point data and the second time-point data, wherein the respective time differences change depending on when the external trigger is acquired, the second time point being after the respective generation time points of the series of gradient magnetic fields, and the eddy magnetic field being resulting from the series of gradient magnetic fields; calculate a frequency variation or phase variation of an MR signal caused by the eddy magnetic field at the second time point from the estimated value of the eddy magnetic fields; and correct a frequency or phase of at least one of an RF transmitting signal to be applied to an object and the MR signal emitted from the object, by using the calculated frequency variation or the phase variation.

Figure 1:
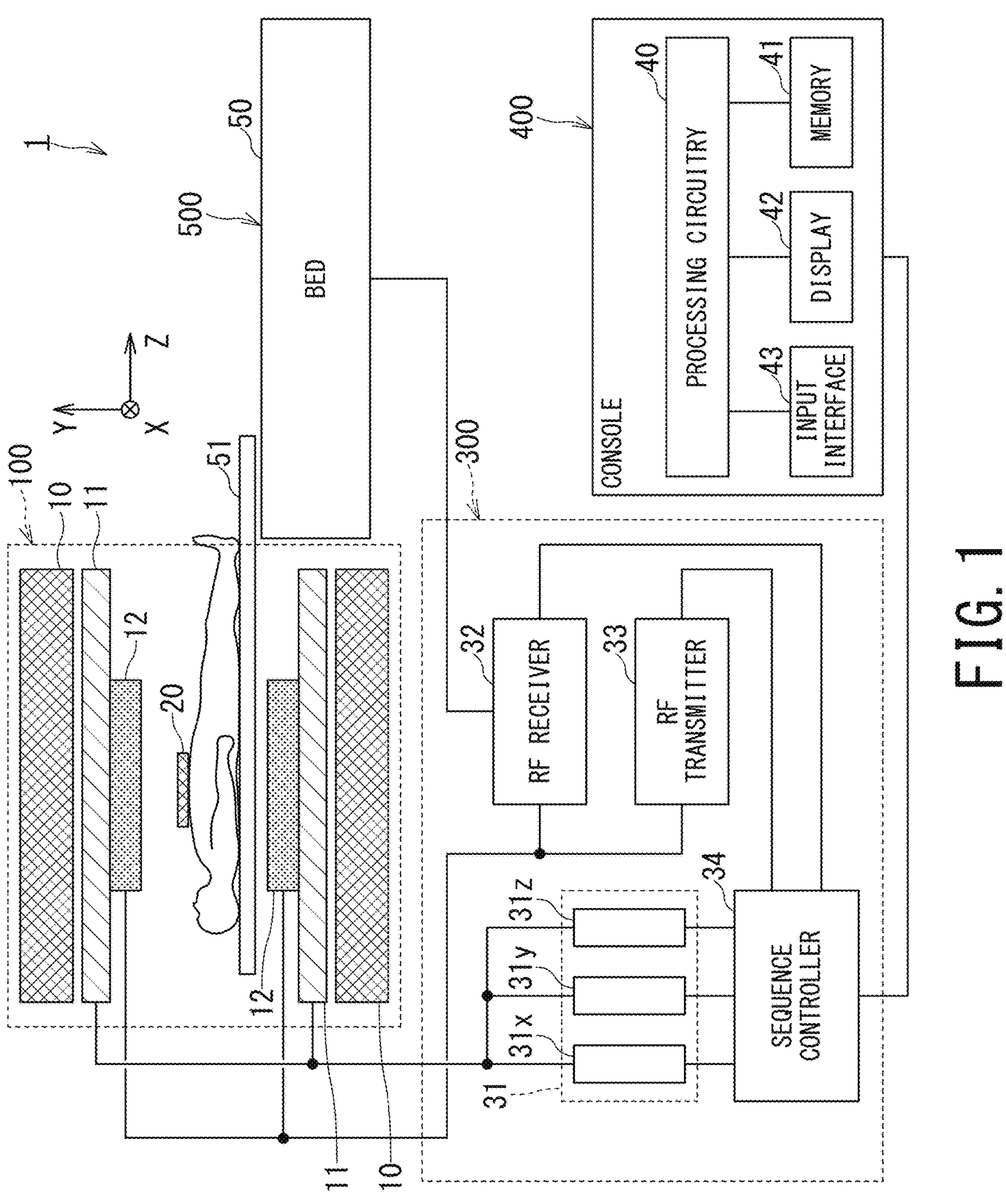
FIG. 1 is a schematic diagram illustrating a configuration of an MRI apparatus according to one embodiment.

FIG. 1 is a block diagram illustrating an overall configuration of an MRI apparatus 1 according to one embodiment.

The MRI apparatus 1 includes a gantry 100, a control cabinet 300, a console 400, a bed 500, and at least one RF (Radio Frequency) coil 20.

The gantry 100 includes a static magnetic field magnet 10, a gradient coil 11, and a whole body (WB) coil 12, and these components are housed in a cylindrical housing.

The bed 500 includes a bed body 50 and a table 51.

The control cabinet 300 includes three gradient-coil power supplies 31 (31*x* for the X-axis, 31*y* for the Y-axis, and 31*z* for the Z-axis), an RF receiver 32, an RF transmitter 33, and a sequence controller 34.

The console 400 includes processing circuitry 40, a memory 41, a display 42, and an input interface 43. The console 400 functions as a host computer.

The static magnetic field magnet 10 of the gantry 100 is substantially in a cylindrical shape, and generates a static magnetic field inside a bore into which an object such as a patient is moved. The bore is a space inside the cylindrical structure of the gantry 100. The static magnetic field magnet 10 has a built-in superconducting coil, and the superconducting coil is cooled down to an extremely low temperature by liquid helium. The static magnetic field magnet 10 generates a static magnetic field by having the superconducting coil supplied with an electric current from a static magnetic field power supply (not shown) in an excitation mode. Afterward, the static magnetic field magnet 10 shifts to a persistent current mode, and the static magnetic field power supply is disconnected. Once it enters the persistent current mode, the static magnetic field magnet 10 continues to generate a strong static magnetic field for a long time, for example, over one year.

The static magnetic field magnet 10 houses the liquid helium and the superconducting coil by using a cylindrical heat shield plate made of an alloy such as aluminum in order to maintain an extremely low temperature state.

The gradient coil 11 is also substantially in a cylindrical shape and is fixed to the inside of the static magnetic field magnet 10. This gradient coil 11 applies gradient magnetic fields to the object in the respective directions of the X-axis, the Y-axis, and the Z-axis by electric currents supplied from the respective gradient-coil power supplies 31*x*, 31*y*, and 31*z*.

The bed body 50 of the bed 500 can move the table 51 in the vertical direction and the horizontal direction. The bed body 50 moves the table 51 with the object placed thereon to a predetermined height before imaging. Afterward, when the object is being imaged, the bed body 50 moves the table 51 in the horizontal direction so as to move the object to the inside of the bore.

The WB body coil 12 is substantially in a cylindrical shape and fixed to the inside of the gradient coil 11 so as to surround the object. The WB coil 12 applies RF pulses transmitted from the RF transmitter 33 to the object. Further, the WB coil 12 receives magnetic resonance signals, i.e., MR signals emitted from the object caused by excitation of hydrogen nuclei.

The MRI apparatus 1 includes one or more RF coils 20 in addition to the WB coil 12 as shown in FIG. 1. Each RF coil 20 is a coil to be disposed close to the body surface of the object. There are various types of the RF coil 20. For example, as shown in FIG. 1, there are a body coil to be attached to the chest, abdomen, or legs of the object and a spine coil to be attached to the back side of the object. Although most of the RF coils 20 are dedicated to reception, some of the RF coils 20 are configured to perform both transmission and reception. Each RF coil 20 is configured to be attachable to and detachable from the table 51 via a cable.

The RF transmitter 33 amplifies a transmitting signal outputted from the sequence controller 34, i.e., an RF pulse. The amplified RF pulse is transmitted to the WB coil 12 and applied to the object. An MR signal is generated from the object by application of the RF pulse. Each MR signal is received by the RF coil 20 or the WB coil 11.

Each MR signal received by the RF coil 20 is inputted to the RF receiver 32 via a cable provided on the table 51 and the bed body 50, for example.

The RF receiver 32 amplifies each MR signal that is an analogue signal, and then outputs each amplified MR signal to the sequence controller 34.

Under the control of the console 400, the sequence controller 34 generates a gradient magnetic field signal (i.e., gradient magnetic field data) to be outputted to the gradient-coil power supplies 31 and an RF pulse to be outputted to the RF transmitter 33 (hereinafter referred to as an RF transmitting signal or simply a transmitting signal) on the basis of various data regarding the pulse sequence required for a scan of the object. The sequence controller 34 performs A/D (Analog to Digital) conversion on the MR signals outputted from the RF receiver 32 such that the MR signals become digital MR signals, and further generates baseband complex MR signals. The MR signals of the baseband complex signals are also referred to as raw data or k-space data.

Furthermore, the sequence controller 34 of the embodiment performs processing for suppressing the frequency variation (or phase variation) of each MR signal caused by the above-described eddy magnetic fields. The processing to be performed by the sequence controller 34 will be described below in detail.

The console 400 controls the entirety of the MRI apparatus 1, such as setting and changing imaging protocols including imaging conditions and/or pulse sequences for imaging the object and giving an instruction to start and finish imaging, as well as displays and stores the MR images. The console 400 includes a memory 41, a display 42, an input interface 43, and processing circuitry 40.

The memory 41 is a recording medium including a read-only memory (ROM) and a random access memory (RAM) in addition to an external memory device such as a hard disk drive (HDD) and an optical disc device. The memory 41 stores various programs to be executed by a processor of the processing circuitry 40 as well as various data and information.

The display 42 is a display device such as a liquid crystal display panel, a plasma display panel, and an organic EL panel.

The input interface 43 includes various devices for a user to input various data and information, such as a mouse, a keyboard, a trackball, and a touch panel.

The processing circuitry 40 is, for example, a circuit provided with a central processing unit (CPU) and/or a special-purpose or general-purpose processor. The processor implements various functions by executing the programs stored in the memory 41. The processing circuitry 40 may be configured as hardware such as a field programmable gate array (FPGA) and an application specific integrated circuit (ASIC). The various functions can also be implemented by such hardware. Additionally, the processing circuitry 40 can implement the various functions by combining hardware processing and software processing based on its processor and programs.

FIG. 2 is a block diagram illustrating a configuration and functions of the sequence controller 34. FIG. 2 is a block diagram that particularly focuses on processing for suppressing frequency variations (or phase variations) of respective MR signals caused by the eddy magnetic fields.

As shown in FIG. 2, the sequence controller 34 includes processing circuitry 340. This processing circuitry 340 implements various functions shown in FIG. 2.

The processing circuitry 340 is a circuit provided with a CPU and/or a special-purpose or general-purpose processor. This processor implements various functions by executing the programs stored in a memory (not shown). The number of CPUS and processors is not specifically limited and may be one or two or more. The processing circuitry 340 may be configured as hardware such as one or more FPGAs and/or one or more ASICS. The various functions shown in FIG. 2 can also be implemented by such hardware. Additionally, the processing circuitry 340 can implement the various functions by combining hardware processing and software processing based on its processor and programs.

It is well known that an eddy magnetic field is generated when a gradient magnetic field pulse (hereinafter abbreviated as a gradient pulse) is applied to the gradient coil 11 of the MRI apparatus 1. When a gradient pulse is applied to the cylindrical gradient coil 11, gradient magnetic fields are generated not only inside the gradient coil 11 but also outside the gradient coil 11. The magnetic field generated outside the gradient coil 11 is so-called a leakage magnetic field. When this leakage magnetic field interlinks with the heat shield plate of the static magnetic field magnet 10, an eddy current will flow through the heat shield plate because the heat shield plate is a conductor.

Each eddy current generates an eddy magnetic field. The generated eddy magnetic fields are superimposed on the gradient magnetic field and the static magnetic field, and thereby disturb the originally expected magnetic field environment, which results in deterioration in image quality. Hence, in order to suppress generation of the eddy currents, an active shielded gradient coil (ASGC) is provided outside the gradient coil 11 for canceling the leakage magnetic field. The gradient coil 11 shown in FIG. 1 may also be configured as the active shielded gradient coil 11.

Although the eddy currents can be suppressed by the active shielded gradient coil 11, it is difficult to make the eddy currents zero. Accordingly, it is important to suppress the influence of the eddy magnetic fields.

Eddy magnetic field can be classified into a magnetic field component independent of the spatial position and another magnetic field component depending on the spatial position. The eddy magnetic field component independent of the spatial position is referred to as the zeroth-order component of the eddy magnetic field, or simply referred to as a zeroth-order eddy magnetic field. On the other hand, the eddy magnetic field component changing as a function of first order or higher order than first order with respect to the spatial position is hereinafter referred to as the first-or-higher order component of the eddy magnetic field.

The first-or-higher order component of the eddy magnetic field causes a variation in the gradient magnetic field strength. When the gradient magnetic field strength varies or fluctuates, problems such as an error in the pixel position occur. In order to correct the first-or-higher order component of the eddy magnetic field, a method of correcting the waveform shape of the gradient pulse is known.

On the other hand, the zeroth-order component of the eddy magnetic field can be regarded as an offset with respect to the static magnetic field strength, and may cause a variation or fluctuation of the magnetic resonance frequency (i.e., the Larmor frequency). Although the zeroth-order component of the eddy magnetic field shows the same value in space, it varies in time.

In a known method for suppressing such a variation in the zeroth-order component of the eddy magnetic field, for example, the variation in the magnetic resonance frequency at a certain time point is calculated from the value obtained by preliminarily integrating the eddy magnetic fields resulting from a series of gradient magnetic fields applied in the past before this certain time point (i.e., the integrated eddy magnetic fields).

However, when imaging is performed in synchronization with an external trigger signal such as an ECG (electrocardiogram) signal, the start timing of the pulse sequence, including the application timing of the gradient magnetic field, changes depending on the occurrence timing of the external trigger signal. Hence, the integrated eddy magnetic fields dynamically changes depending on the occurrence timing of the external trigger, and thus, the integrated eddy magnetic fields cannot be accurately calculated. As a result, there is a problem that the variation amount in the magnetic resonance frequency cannot be accurately calculated, and therefore deterioration in image quality caused by the variation in the magnetic resonance frequency cannot be sufficiently suppressed.

As shown below, the sequence controller 34 of the MRI apparatus 1 of the present embodiment has a function to solve the above-described problem.

As shown in FIG. 2, the processing circuitry 340 of the sequence controller 34 implements each of a time-point data generation function F01, a gradient-magnetic-field data/signal generation function F02, an eddy-magnetic-field estimation function F03, a frequency/phase variation calculation function F04, a transmitting processing function F05, a receiving processing function F06, a pulse-sequence data setting function F07, a control function F08, and a reconstruction processing function F09. The transmitting processing function F05 includes a transmitting-signal generation function F51 and a transmitting-signal correction function F52 as its subordinate configuration. The receiving processing function F06 includes a receiving function F61 and a receiving-signal correction function F62 as its subordinate configuration.

The time-point data generation function F01 continuously generates time-point data in increments of a predetermined time length. For example, the time-point data generation function F01 generates the time-point data where the start timing of imaging is defined as 0 seconds, and the time-point data continuously increase in increments of time shorter than 1 microsecond (for example, in increments of nanoseconds according to the order). The generation method of the time-point data is not limited to a specific method. For example, the processor may sequentially generate the time-point data. Alternatively, the time-point data may be generated by counting up a clock signal with a predetermined frequency.

The pulse-sequence data setting function F07 sets parameter values related to RF pulses and gradient pulses as pulse sequence data in accordance with the type of pulse sequence to be applied to the object on the basis of instructions from the console 400. These pulse sequence data (i.e., parameter values) are set on the gradient-magnetic-field data/signal generation function F02, the transmitting processing function F05, and the receiving processing function F06.

The gradient-magnetic-field data/signal generation function F02 generates a series of gradient magnetic field data or gradient magnetic field signals based on the predetermined pulse sequence in association with a series of time-point data (hereinafter referred to as a series of first time-point data), which are generated by the time-point data generation function F01 and correspond to respective generation time points of the series of gradient magnetic fields based on the predetermined pulse sequence.

The series of generated gradient magnetic field signals are converted into predetermined gradient magnetic field currents by the gradient-coil power supplies 31, applied to the gradient coil, and outputted to the eddy-magnetic-field estimation function F03.

The eddy-magnetic-field estimation function F03 estimates an eddy magnetic field (i.e., a strength value of an integrated magnetic field of the eddy magnetic fields) at a second time point, which is caused by the series of gradient magnetic fields, by using: the series of gradient magnetic field data generated by the gradient-magnetic-field data/signal generation function F02; the series of first time-point data generated by the time-point data generation function F01; and the second time-point data corresponding to the second time point after the respective generation time points of the series of gradient magnetic fields. As described below, the second time point corresponds to a generation time point of an RF transmitting signal or a sampling time point of a receiving signal.

The frequency/phase variation calculation function F04 calculates the frequency variation or phase variation of the MR signal caused by the eddy magnetic field at the second time point from the estimated value of the eddy magnetic fields.

The transmitting-signal generation function F51 of the transmitting processing function F05 generates the RF transmitting signal in association with the above-described second time-point data on the basis of the predetermined pulse sequence (for example, on the basis of the pulse sequence data outputted from the pulse-sequence data setting function F07). The RF transmitting signal is an RF pulse that has a predetermined magnetic resonance frequency and a predetermined envelope.

The RF transmitting signal can be generated by using a DDS (Direct Digital Synthesizer). In the DDS, a signal corresponding to the magnetic resonance frequency is directly generated as digital data, and then generated as the RF transmitting signal by D/A conversion. Instead of such digital processing, the RF transmitting signal may be generated through analog processing. For example, the RF transmitting signal having the magnetic resonance frequency may be generated by: (i) generating a baseband pulse signal with a predetermined envelope as an analog signal through D/A conversion; and then (ii) up-converting the baseband pulse signal with a local signal having a predetermined frequency.

The transmitting-signal generation function F51 can generate the RF transmitting signal that includes at least one of an excitation pulse, an inversion pulse, a refocusing pulse, and a labeling pulse, as a relatively broadband RF pulse including both a water excitation pulse and a fat suppression pulse. The transmitting-signal generation function F51 can also generate the RF transmitting signal that has narrower bandwidth than each of the above-described RF pulses and includes either or both of the fat suppression pulse and the water excitation pulse. The fat suppression pulse is an RF pulse having the magnetic resonance frequency of fat as center frequency. The water excitation pulse is an RF pulse having the magnetic resonance frequency of water as center frequency.

The transmitting-signal correction function F52 of the transmitting processing function F05 generates the RF transmitting signal by using the estimated value of the eddy magnetic fields for correcting the frequency or phase of the RF transmitting signal in such a manner that the variations in the frequency or phase of the respective MR signals caused by the eddy magnetic fields are suppressed.

The correction of the frequency or phase of the RF transmitting signal may be performed on the baseband analog signal or on the local signal to be used for up-conversion. When the RF transmitting signal is generated by using the DDS, it is sufficient to correct the frequency or phase of the signal as digital data.

The receiving processing function F06 uses the estimated value of the eddy magnetic fields to convert the frequency of the MR signals received by the RF coil 20 and/or WB coil 12 into the baseband, or to correct the frequency or phase of the MR signals having been converted into the baseband, such that the variations in the frequency or phase of the respective MR signals caused by the eddy magnetic fields are suppressed.

More specifically, the receiving processing function F06 corrects the frequency of the local signal to be applied for converting the frequency of the MR signals into the baseband in the analog domain or digital domain, such that the variations in the frequency or phase of the respective MR signals caused by the eddy magnetic fields are suppressed.

Alternatively, the receiving processing function F06 may correct the frequency or phase of the converted baseband MR signals (i.e., k-space data) by digital calculation, in such a manner that the variations in the frequency or phase of the respective MR signals caused by the eddy magnetic fields are suppressed.

The reconstruction processing function F09 reconstructs an MR image by performing reconstruction processing such as inverse Fourier transform on the MR signals (i.e., k-space data) having been subjected to the frequency correction or phase correction. The reconstruction processing function F09 may be achieved by the processing circuitry 40 of the console 400 instead of the sequence controller 34.

The control function F08 performs overall control of the sequence controller 34.

The operations of each of the above-described functions will be described in more detail by referring to the respective flowcharts of FIG. 3, FIG. 7, FIG. 11, and FIG. 13 as well as FIG. 4A to FIG. 6, FIG. 8A to FIG. 10D, FIG. 12A to FIG. 12G, and FIG. 14A to FIG. 14G as required.

Although the MRI apparatus 1 of the embodiment has the same configuration regardless of whether the external trigger is inputted or not, for facilitating understanding, first, a description will be given of the behavior when the external trigger is not inputted, and then a description will be given of the behavior when the external trigger is inputted.

Figure 3:
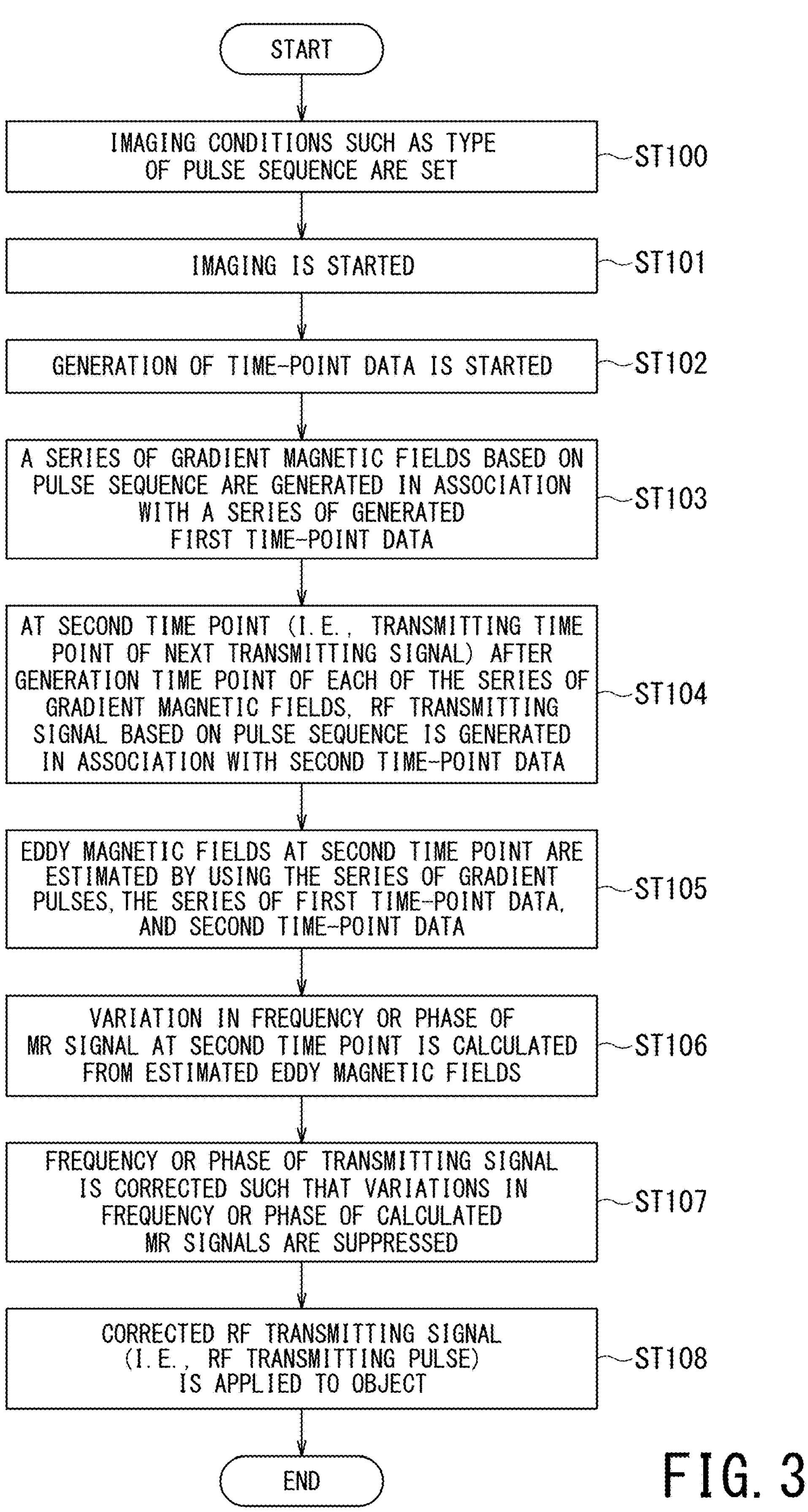
FIG. 3 is a flowchart illustrating transmitting processing when an external trigger is not inputted.

FIG. 3 is a flowchart illustrating transmitting processing when the external trigger is not inputted.

In the first step ST100, imaging conditions such as a type of the pulse sequence are set as pulse sequence data. The processing of the step ST100 is performed by the pulse-sequence data setting function F07.

Figures 4A, 4B, 4C, 4D, 4E, 4F:
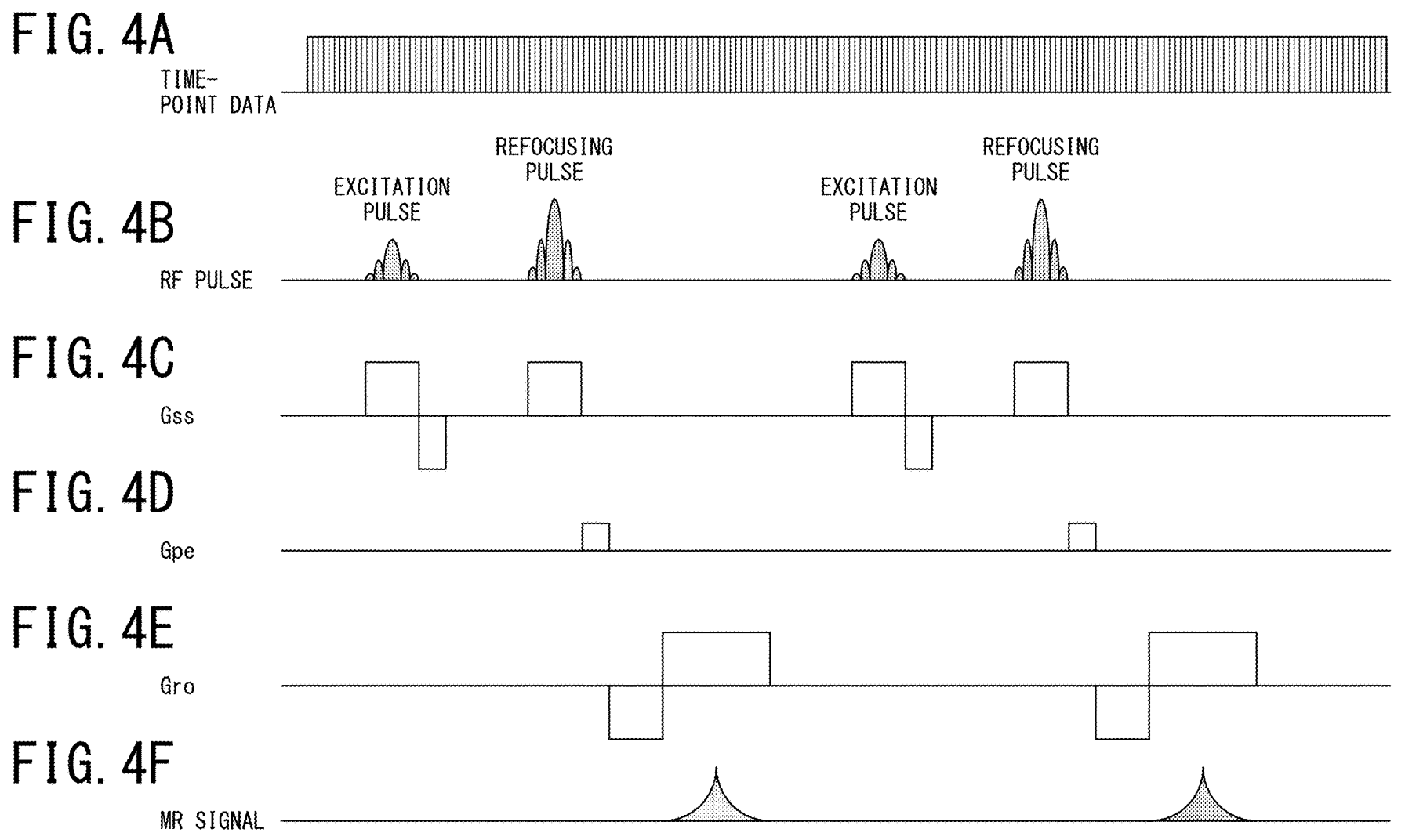

FIG. 4A to FIG. 4F are timing charts illustrating a pulse sequence set by the pulse-sequence data setting function F07 together with time-point data (FIG. 4A) generated by the time-point data generation function F01. FIG. 4A to FIG. 4F illustrate a pulse sequence of a standard spin echo method. FIG. 4B shows RF pulses including excitation pulses and refocusing pulses, FIG. 4C shows slice selection gradient pulses Gss, FIG. 4D shows phase encode gradient pulses Gpe, FIG. 4E shows readout gradient pulses Gro, and FIG. 4F shows MR signals received by the RF coil 20.

The RF pulses shown in FIG. 4B and the respective gradient pulses shown in FIG. 4C to FIG. 4E are generated in association with the time-point data generated by the time-point data generation function F01. Each MR signal shown in FIG. 4F is also sampled at the timing associated with the time-point data generated by the time-point data generation function F01.

There is no limitation to the type of pulse sequence that can be applied to the MRI apparatus 1 of the present embodiment, and any pulse sequence can be used for the MRI apparatus 1 of the present embodiment.

Although a reference for starting generation of the time-point data by the time-point data generation function F01 is not limited to a specific timing, the time-point data generation function F01 may start generating the time-point data by using the start of the imaging as a trigger, as shown in the steps ST101 and ST102, for example.

In the step ST103, as illustrated in FIG. 4C to FIG. 4E, a series of gradient pulses based on the pulse sequence are generated in association with the series of generated first time-point data.

In the next step ST104, at the second time point (i.e., transmitting time point of the next RF transmitting signal) after the generation time point of each of the series of gradient pulses, the RF transmitting signal based on the pulse sequence is generated in association with the second time-point data.

In the next step ST105, the eddy magnetic field at the second time point are estimated by using the series of gradient pulses, the series of first time-point data, and the second time-point data.

FIG. 5A to FIG. 5G are timing charts schematically illustrating both behavior of respective zeroth-order eddy magnetic fields generated by the series of gradient magnetic fields (i.e., gradient pluses) in the time axis and behavior of a variation ΔB(t) in an integrated eddy magnetic field obtained by integrating these zeroth-order eddy magnetic fields.

FIG. 5A, FIG. 5C, and FIG. 5E respectively illustrate part of the slice selection gradient pulse Gss, the phase encode gradient pulse Gpe, and the readout gradient pulse Gro, among the pulse sequence shown in FIG. 4A to FIG. 4F.

The shape of each gradient pulse is actually approximated as a trapezoidal shape rather than a rectangular shape, and eddy magnetic fields are generated so as to cancel the variations of the magnetic field at both the rising edge and falling edge of the trapezoidal shape of the gradient pulse. As described above, each eddy magnetic field includes both the zeroth-order component independent of the spatial position and the first-or-higher order component, which varies as a linear function or varies as a second or higher order function with respect to the spatial position.

FIG. 5B schematically illustrates the waveform of the zeroth-order component of the eddy magnetic field (hereinafter, shortly referred to as the zeroth-order eddy magnetic field) ABss that is generated corresponding to the slice selection gradient pulse Gss. Similarly, FIG. 5D schematically illustrates the waveform of the zeroth-order eddy magnetic field ΔBpe that is generated corresponding to the phase encode gradient pulse Gpe. FIG. 5F schematically illustrates the waveform of the zeroth-order eddy magnetic field ΔBro that is generated corresponding to the readout gradient pulse Gro.

Due to the rising of each gradient pulse, i.e., due to the variation of the gradient magnetic field in the positive direction, the zeroth-order eddy magnetic field of negative polarity is generated so as to cancel this variation, and this zeroth-order eddy magnetic field decays with a function approximated by an exponential function. Meanwhile, due to the falling of each gradient pulse, i.e., due to the variation of the gradient magnetic field in the negative direction, the zeroth-order eddy magnetic field of positive polarity is generated so as to cancel this variation, and this zeroth-order eddy magnetic field also decays with a function approximated by an exponential function.

The time constant of the exponential function may become a large value, for example, from several msec to about 2000 msec. Thus, as illustrated in FIG. 5B, FIG. 5D, and FIG. 5F, the plurality of zeroth-order eddy magnetic fields generated at the rising and falling edges of the respective gradient pulses decay but continue even after the application of the respective gradient pulses.

The time constant of each zeroth-order eddy magnetic field can be obtained in advance from actual measurement data, for example. The strength of each zeroth-order eddy magnetic field can also be estimated in advance from the magnitude of the variation in the rising edge and falling edge of each gradient pulse.

Thus, the plurality of zeroth-order eddy magnetic fields to be generated corresponding to the rising and falling of the series of gradient pulses as shown in FIG. 5B, FIG. 5D, and FIG. 5F can be estimated as functions of time on the basis of type and parameters of the pulse sequence that are set in the step ST100.

The integrated value of the zeroth-order eddy magnetic field ΔB(t) varying every moment can be estimated as a function of time by: integrating strength values of the plurality of zeroth-order eddy magnetic fields having occurred in the past before a certain time point in each of the slice selection direction, the phase encoding direction, and the readout direction; and further integrating the integrated zeroth-order eddy magnetic fields in the slice selection direction, the phase encoding direction, and the readout direction, as shown in FIG. 5G.

As described above, the MRI apparatus 1 of the present embodiment generates the series of gradient pulses based on the pulse sequence in association with the series of first time-point data. The series of first time-point data are the time-point data associated with each of the slice selection gradient pulse Gss, the phase encode gradient pulse Gpe, and the readout gradient pulse Gro among the time-point data generated by the time-point data generation function F01. For example, the series of first time-point data are the time-point data corresponding to the rising and falling of each gradient pulse.

Furthermore, the time of interest after the respective generation time points of the series of gradient magnetic fields (i.e., the time point at which the integrated value of the zeroth-order eddy magnetic field ΔB(t) is to be calculated) is defined as the second time point. In this case, respective strength values of the series of exponentially decaying eddy magnetic fields at the second time point can be calculated by using both the strength of each of the series of gradient magnetic fields and the respective time differences between the above-described series of first time-point data and the second time-point data corresponding to the second time point. Further, the strength value of the zeroth-order eddy magnetic field ΔB at the second time point as the time of interest can be calculated by integrating all the calculated strength values of the eddy magnetic fields at the second time point as described above.

Since the waveform of each zeroth-order eddy magnetic field is approximated as an exponential function, once the zeroth-order eddy magnetic field is generated, this zeroth-order eddy magnetic field does not become completely zero even after elapse of a long period of time. For this reason, when calculating the integrated value of the zeroth-order eddy magnetic field ΔB(t), the plurality of zeroth-order eddy magnetic fields generated by the gradient pulses applied for the predetermined past Tpast seconds immediately before the second time point are integrated.

FIG. 6A to FIG. 6F are timing charts illustrating a processing concept of the steps ST103 to ST105 when the time of interest (i.e., the second time point) is immediately before or during transmission of the RF transmitting signal.

FIG. 6A, FIG. 6B, FIG. 6C, and FIG. 6D are timing charts respectively corresponding to FIG. 4A, FIG. 4C, FIG. 4D, and FIG. 4E. FIG. 6E is a diagram corresponding to FIG. 5G, and schematically illustrates the temporal change in the integrated value of the zeroth-order eddy magnetic field ΔB(t).

Figures 6A, 6B, 6C, 6D, 6E, 6F:
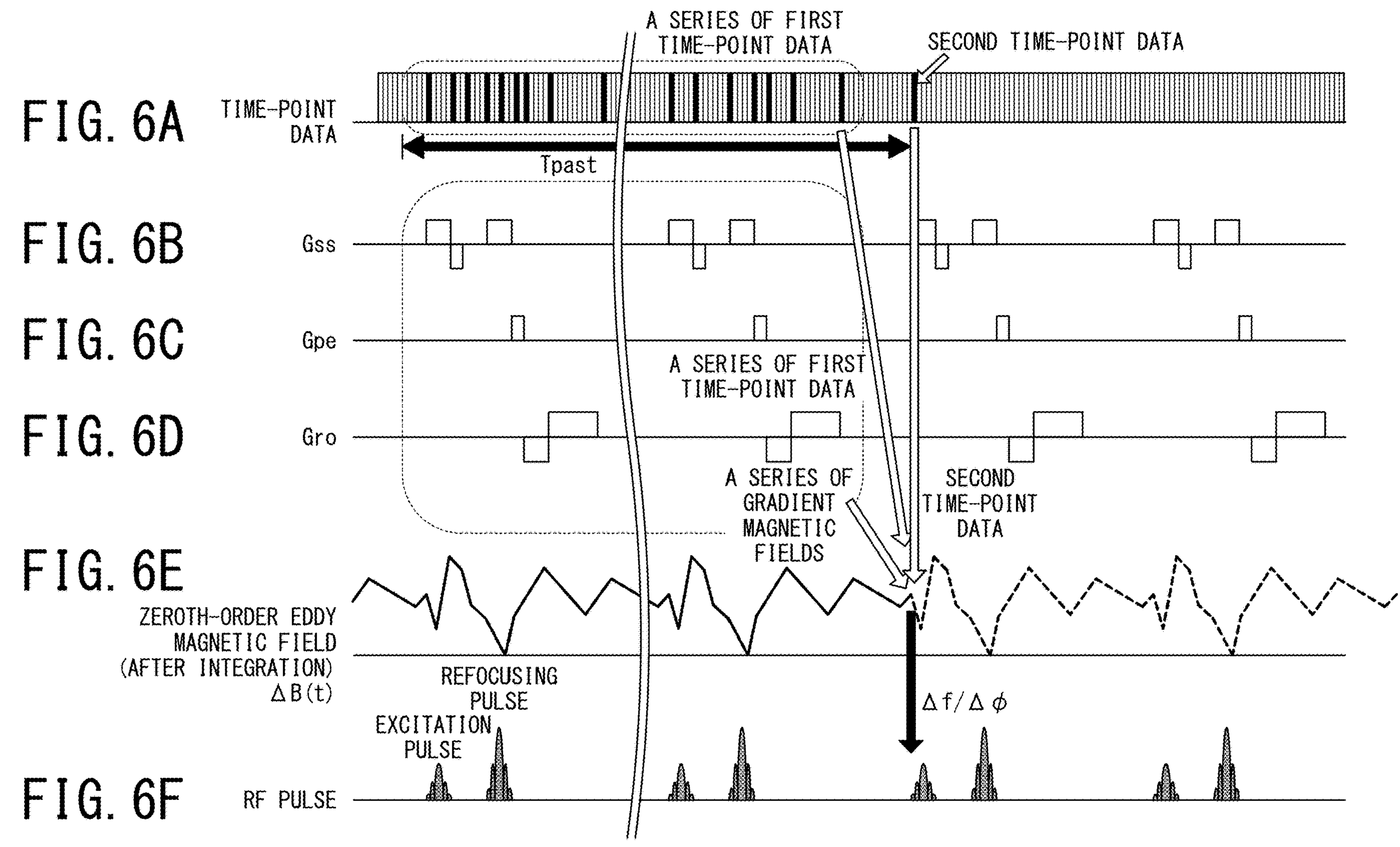
FIG. 6A to FIG. 6F are timing charts illustrating a processing concept of estimating eddy magnetic fields when a time of interest (i.e., a second time point) is in a transmitting period of an RF transmitting signal.

FIG. 6F is a timing chart illustrating generation of the RF pulses, and FIG. 6F illustrates a case where the excitation pulse and the refocusing pulse are repeatedly generated at intervals of the repetition time TR.

FIG. 6A to FIG. 6F show a situation where the time point immediately before generation of the third excitation pulse, that is the third one from the left shown in FIG. 6F, is treated as the time of interest (i.e., the second time point), and the zeroth-order eddy magnetic fields at this second time point are calculated. In this case, the zeroth-order eddy magnetic fields at this second time point are calculated by using: the series of gradient pulses generated in the period between the second time point and the time point before the second time by a predetermined time length Tpast; a series of first time points associated with this series of gradient pulses; and the second time point.

In the time-point data shown in FIG. 6A, each of the sequentially increasing time-point data is represented by white vertical stripes among these time-point data, the series of first time-point data corresponding to the respective generation time points of the series of gradient magnetic fields (i.e., the rising time points and falling time points of the series of gradient pulses) are indicated by thick black vertical stripes.

Returning to FIG. 3, when the time of interest (i.e., the second time point) is defined as Ttoi, the zeroth-order eddy magnetic field ΔB(t) estimated in the step ST105 of FIG. 3 is expressed as ΔB(Ttoi).

In the step ST106 of FIG. 3, the variation in the frequency or phase of the MR signal at the second time point is calculated from the estimated eddy magnetic fields. For example, the frequency variation Δf(Ttoi) of the magnetic resonance frequency at the second time point (i.e., the time of interest Ttoi) can be calculated from the estimated eddy magnetic field ΔB(Ttoi) by using the following Expressions 1 to 4.

$$B(Ttoi) = B_0 + \Delta B(Ttoi) \quad \text{Expression 1}$$

$$f(Ttoi) = f_0 + \Delta f(Ttoi \quad \text{Expression 2}$$

$$f_0 = \lambda \cdot B_0/(2\pi) \quad \text{Expression 3}$$

$$\Delta f(Ttoi) = \lambda \cdot \Delta B(Ttoi)/(2\pi) \quad \text{Expression 4}$$

In Expressions 1 to 4, $B_0$ is the static magnetic field strength, $f_0$ is the magnetic resonance frequency determined only by the static magnetic field strength $B_0$, and λ is a constant called a gyromagnetic ratio.

The phase variation Δφ(Ttoi), which has a one-to-one correspondence with the frequency variation Δf(Ttoi), may be calculated from the frequency variation Δf(Ttoi).

In the step ST107 of FIG. 3, the frequency or phase of the transmitting signal is corrected in such a manner that the variation in the frequency or phase of the calculated MR signal is suppressed. As described above, this correction is performed by the transmitting-signal correction function F52 of the transmitting processing function F05.

In the step ST108, the corrected RF transmitting signal (i.e., RF transmitting pulse) is applied to the object. The foregoing is one aspect of the transmitting processing when the external trigger is not inputted.

Figure 7:
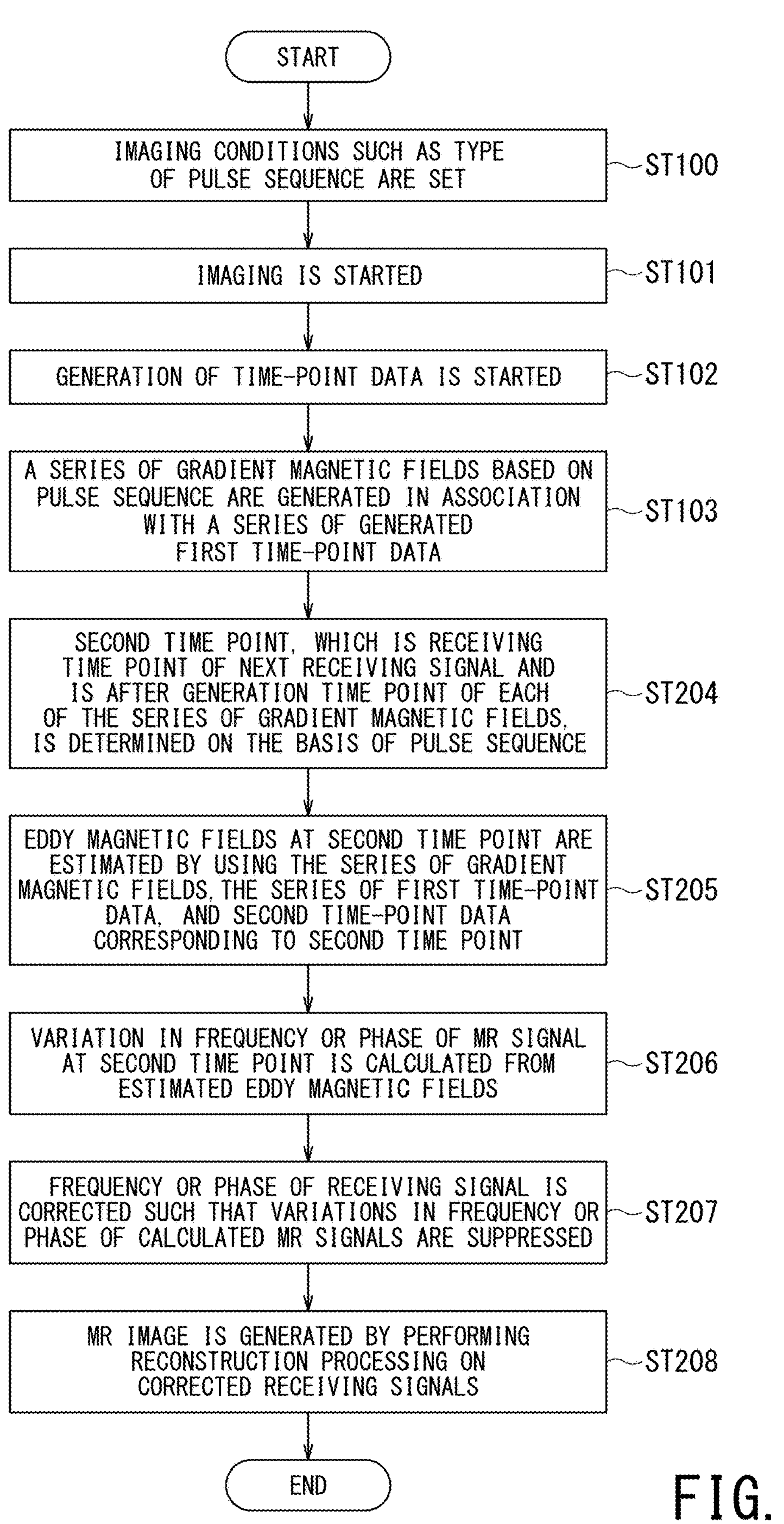
FIG. 7 is a flowchart illustrating receiving processing when the external trigger is not inputted.
Figures 8A, 8B, 8C, 8D, 8E, 8F:
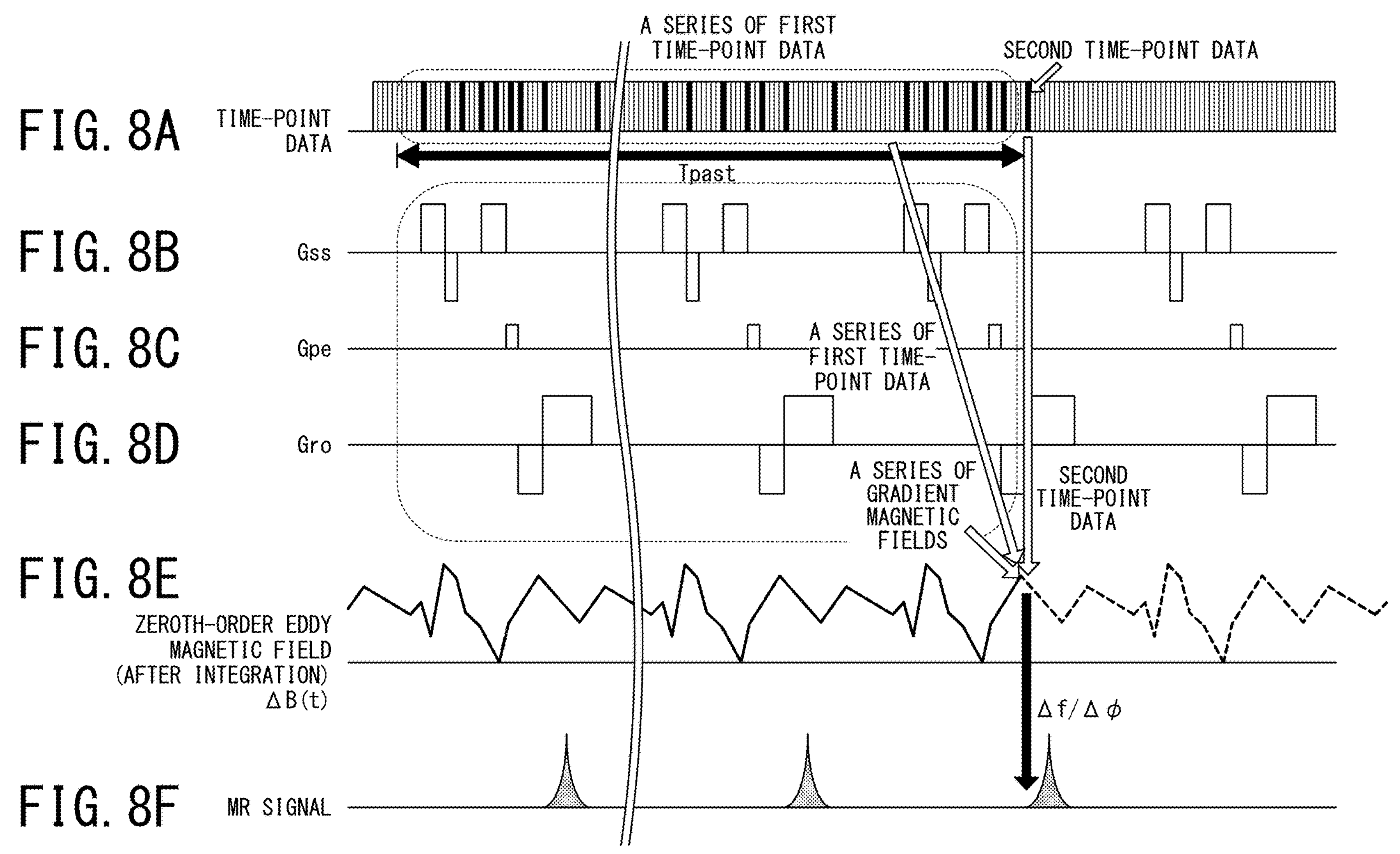
FIG. 8A to FIG. 8F are timing charts illustrating a processing concept of estimating eddy magnetic fields when the time of interest (i.e., the second time point) is in a receiving period of an MR signal.

In the meantime, FIG. 7 is a flowchart illustrating "receiving" processing when the external trigger is not inputted. The steps ST100 to ST103 are the same as those in FIG. 3, which illustrates the "transmitting" processing, and duplicate descriptions are omitted.

In the step ST204, the second time point, which is the receiving time point when the next receiving signal is received after the generation time point of each of the series of gradient pulses, is determined on the basis of the pulse sequence.

In the next step ST205, the eddy magnetic fields at the second time point are estimated by using the series of gradient magnetic fields, the series of first time-point data, and the second time-point data corresponding to the second time point.

FIG. 8A to FIG. 8F are timing charts illustrating a processing concept of the steps ST204 and ST205. In the receiving processing, the time of interest (i.e., the second time point) corresponds to the start time of receiving the MR signal or corresponds to the time point during the receiving period (i.e., sampling period) of the MR signal.

In the receiving processing shown in FIG. 8A to FIG. 8E, the time of interest (i.e., the second time point) corresponds to the start time point of receiving the MR signal (or corresponds to the time point during the sampling period of the MR signal), which is different from the transmitting processing shown in FIG. 6A to FIG. 6E where the time of interest (i.e., the second time point) corresponds to the transmitting time point of the RF transmitting signal. Except this difference, FIG. 8A to FIG. 8E are the substantially the same as FIG. 6A to FIG. 6E, and the method for estimating the zeroth-order eddy magnetic field ΔB(Ttoi) at the time of interest (i.e., the second time point) Ttoi in the receiving processing is substantially the same as the method described in the transmitting processing.

In the step ST206 of FIG. 7, the frequency variation or phase variation (Δf(Ttoi) or Δφ(Ttoi)) of the MR signal at the time of interest (i.e., the second time point) is calculated from the estimated zeroth-order eddy magnetic field ΔB(Ttoi). This calculation method is the same as the method described in the transmitting processing, and can be achieved by using Expressions 1 to 4.

In the step ST207, the frequency or phase of the receiving signal is corrected in such a manner that the calculated frequency or phase variation of the MR signal is suppressed.

Figure 9:
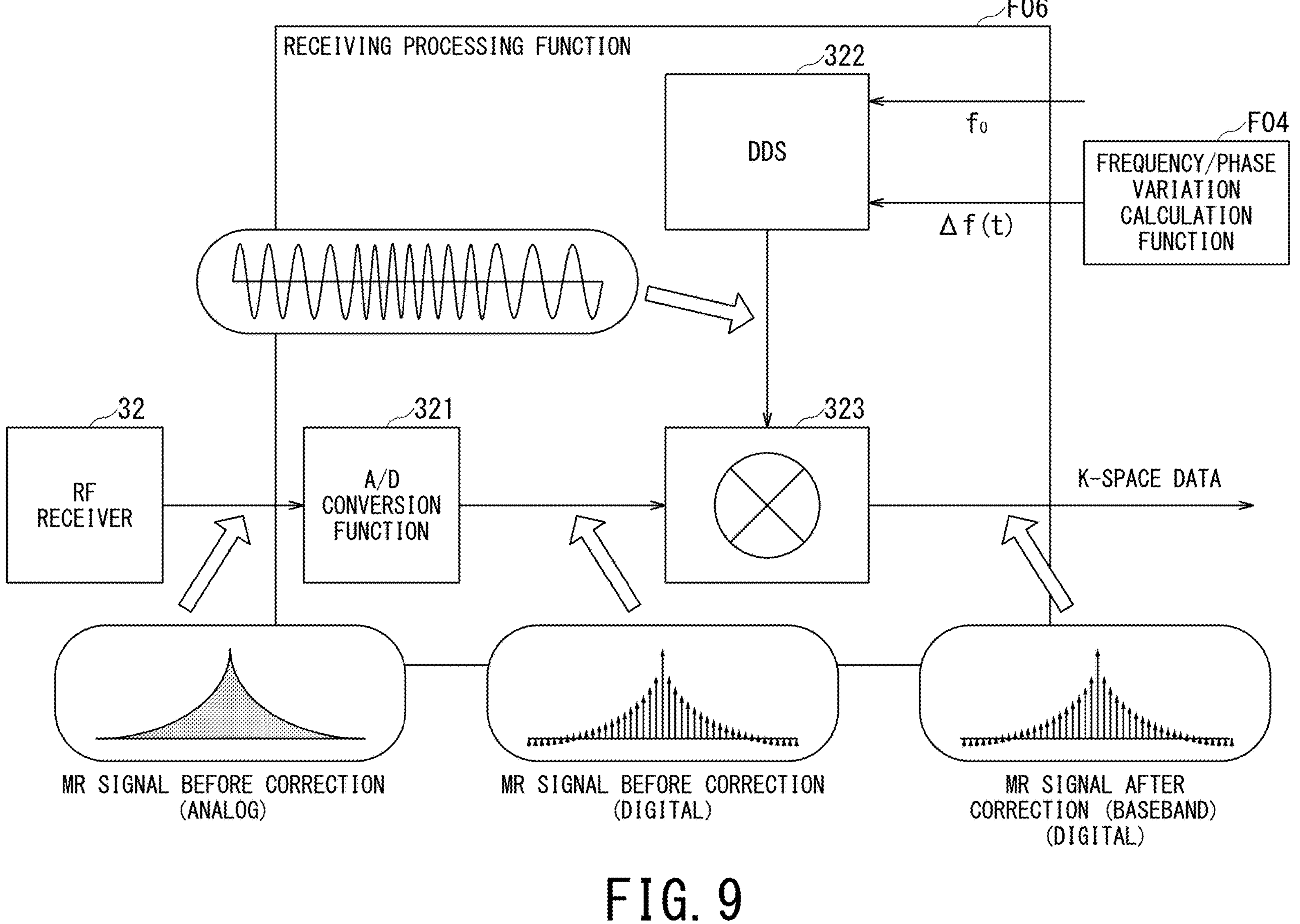
FIG. 9 is a schematic diagram illustrating a concept of a first method for correcting a frequency or phase of the receiving signal.
Figure 10:
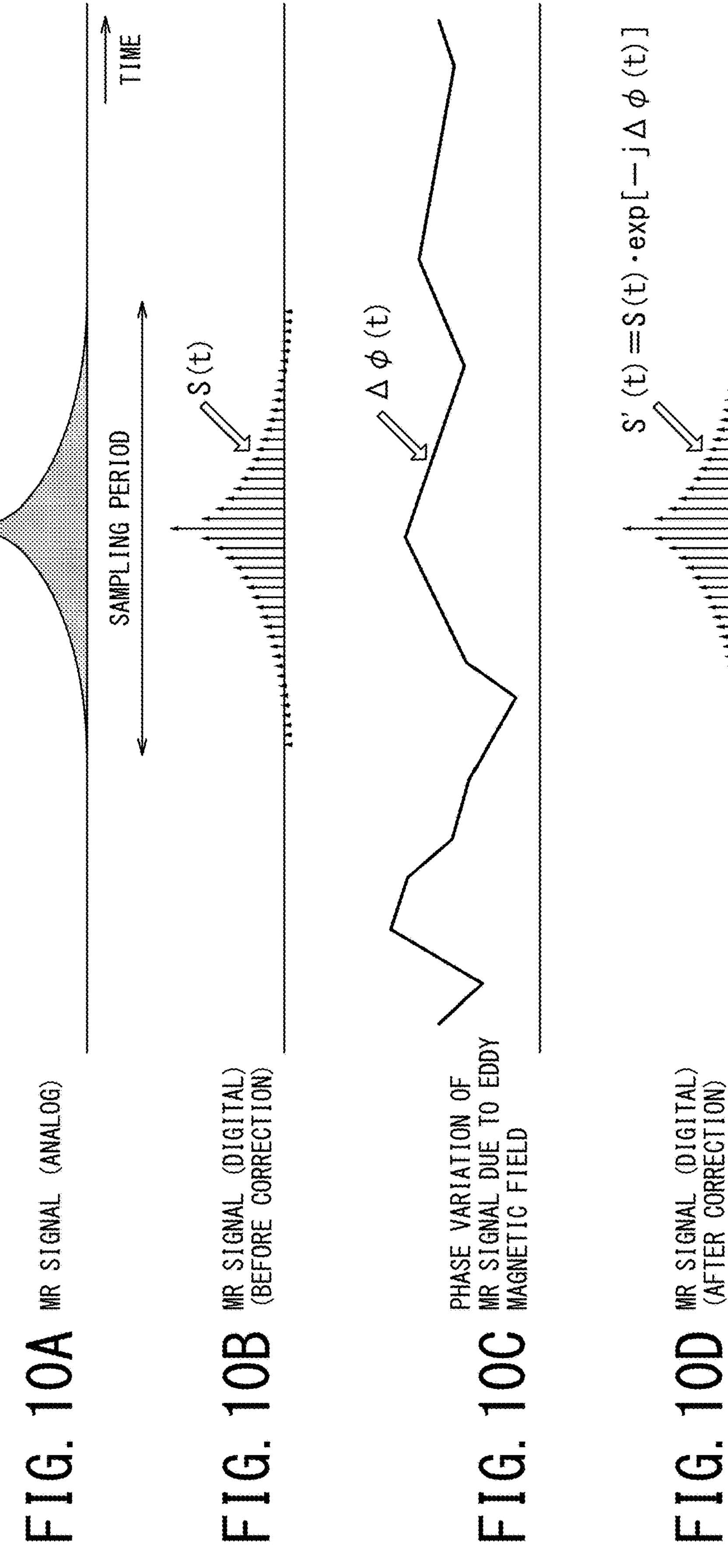
FIG. 10A to FIG. 10D are waveform diagrams illustrating a concept of a second method for correcting the frequency or phase of the receiving signal.

FIG. 9 is a schematic diagram illustrating a concept of a first method for correcting the frequency or phase of the receiving signal. In this first method, the receiving processing function F06 shown in FIG. 2 is achieved by an A/D conversion function 321, a DDS (Direct Digital Synthesizer) function 322, and a wave detection function 323 as shown in FIG. 9.

The receiving processing function F06 illustrated in FIG. 9 corresponds to a so-called direct sampling method. In the direct sampling method, the MR signal amplified by the RF receiver 32 is directly sampled by the A/D conversion function 321 without frequency conversion, and the analog signal is directly converted into a digital signal. Furthermore, in the direct sampling method, the converted digital MR signal is detected by using a reference signal, which has a carrier frequency component and is outputted from the DDS 322, and the detected MR signal is converted to a baseband digital MR signal. This baseband digital MR signal is, for example, a complex signal composed of an I signal and a Q signal, and is sometimes called raw data or k-space data as described above.

In the first method of the correction processing, the DDS 322 is configured such that the frequency of the reference signal outputted from the DDS 322 changes to follow the variations in the eddy magnetic fields. As a result, in the output of the wave detection function 323, the frequency variation caused by the variations of the eddy magnetic fields is canceled out, and the influence of the eddy magnetic fields can be suppressed.

FIG. 10A to FIG. 10D are waveform diagrams illustrating a concept of a second method for correcting the frequency or phase of the receiving signal. In the second method, the frequency variation or phase variation in the receiving signal is corrected by digital calculation on k-space data.

FIG. 10A schematically illustrates the MR signal as an analog signal. FIG. 10B schematically illustrates the MR signal S(t) as a sampled baseband digital signal. The MR signal before correction is expressed as S(t).

FIG. 10C illustrates the phase variation $\Delta\varphi(t)$ obtained by time-integrating the frequency variation $\Delta f(t)$ of the receiving signal. FIG. 10D schematically illustrates the digitized MR signal after correction. When the corrected MR signal is expressed as S'(t), the corrected MR signal is calculated by, for example, Expression 5 below.

$$S'(t)=S(t)\cdot\exp[-j\Delta\varphi(t)] \quad \text{Expression 5}$$

Returning to FIG. 7, in the step ST208 of FIG. 7, an MR image is generated by performing reconstruction processing on the corrected receiving signals (i.e., corrected MR signals).

Although a description has been given of the transmitting processing and the receiving processing for the case where the external trigger is not inputted, in the following, a description will be given of the transmitting processing and the receiving processing for the case where the external trigger is inputted.

The external trigger is, for example, an ECG signal or a respiratory synchronization signal. Imaging using the ECG signal as the external trigger is referred to as cardiac gating imaging. The cardiac gating imaging is an imaging method in which MR signals are acquired at a specific cardiac time phase in synchronization with an ECG signal when imaging the heart, for example. On the other hand, imaging using a respiratory synchronization signal as the external trigger is referred to as respiratory synchronization imaging. When respiration is divided into an expiratory phase and an inspiratory phase, the respiratory synchronization imaging is an imaging method in which MR signals are acquired only during, for example, a specific period in the expiratory phase in synchronization with the respiratory synchronization signal.

In the synchronization imaging method using the external trigger, imaging is started after elapse of a predetermined delay time Tdl from the time point at which the external trigger is inputted, and imaging is stopped when MR signals corresponding to a predetermined number of TRs (pulse repetition periods) are acquired. Afterward, when the next external trigger is inputted, imaging is restarted after elapse of the delay time Tdl from that input time point of the trigger signal, and this operation is repeated every time the external trigger is inputted so as to obtain the MR signals necessary for generating an image.

In normal imaging without using the external trigger, the interval between adjacent excitation pulses (i.e., TR) is always constant. However, the cycle period of the input of external trigger signal such as an ECG signal and a respiratory synchronization signal is not constant but changes. Thus, in the synchronization imaging method using the external trigger signal, the interval between the excitation pulse immediately before input of a certain external trigger signal and the excitation pulse immediately after input of this external trigger signal is not TR but changes depending on the input timing of the external trigger. Similarly, the repetition interval between the gradient magnetic fields in a specific application direction (e.g., the readout direction) is not constant, and the interval between the gradient pulse immediately before input of a certain external trigger signal and the gradient pulse immediately after input of this external trigger signal changes depending on the input timing of the external trigger.

The MRI apparatus 1 of the embodiment can accurately calculate the eddy magnetic fields at the time of interest even in such an imaging method in which periodicity cannot be kept before and after the input of the external trigger, as described below using FIG. 11 to FIG. 14G.

The external trigger can be obtained by the control function F08 of the processing circuitry 340, for example. The control function F08 acquires the external trigger in association with trigger-time-point data, which are time-point data generated by the time-point data generation function F01 and correspond to an acquisition time point of each external trigger.

Figure 11:
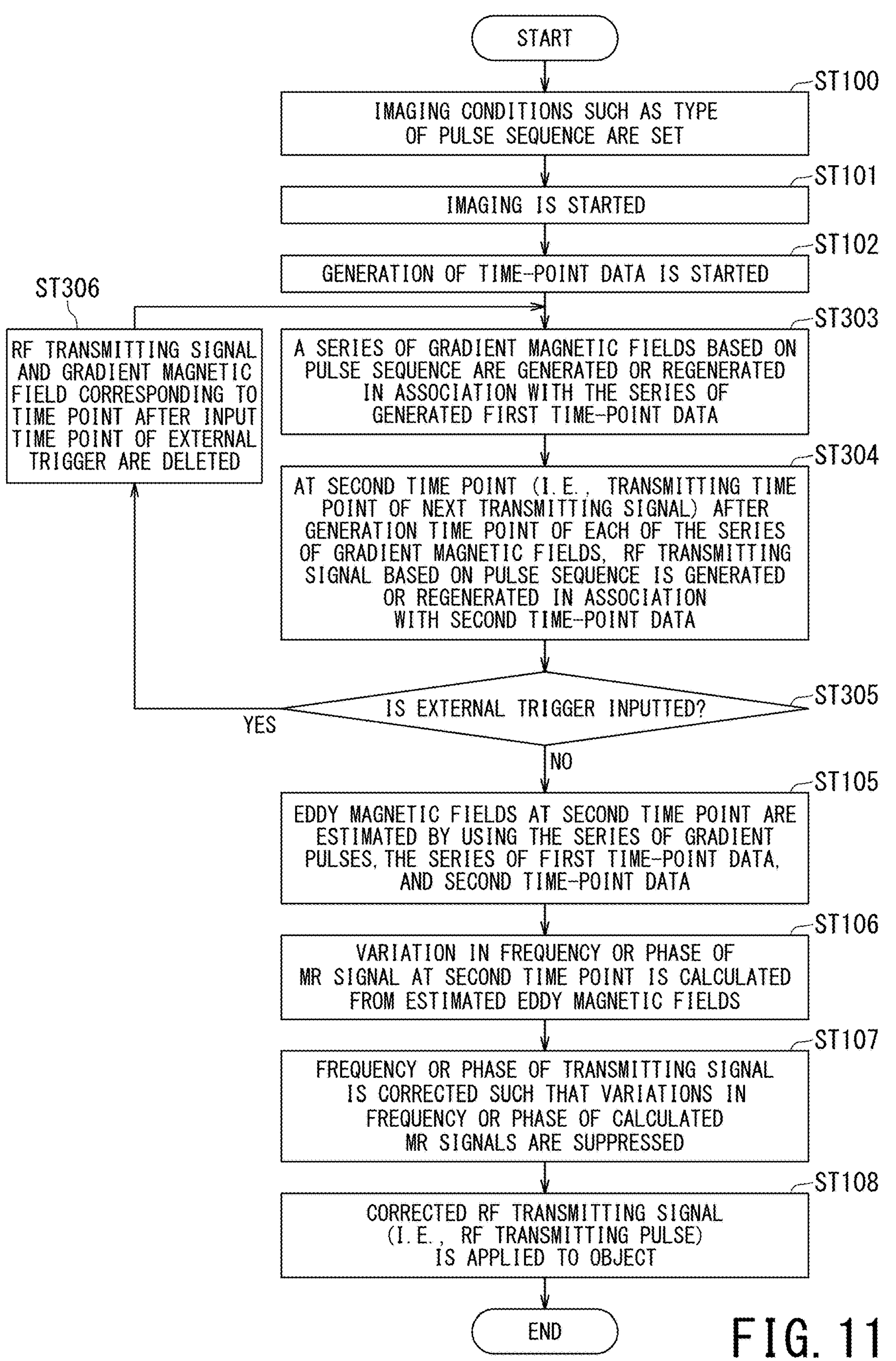
FIG. 11 is a flowchart illustrating transmitting processing when the external trigger is inputted.

FIG. 11 is a flowchart illustrating transmitting processing when the external trigger is inputted.

The steps ST100 to ST102 in FIG. 11 are the same as the case where the external trigger is not inputted, and duplicate descriptions are omitted.

In the step ST303, a series of gradient magnetic fields based on the pulse sequence are generated or regenerated in association with a series of first time-point data.

The MRI apparatus 1 of the embodiment uses a method that generates a series of gradient magnetic fields based on the pulse sequence in association with time-point data. Thus, Data for generating a series of gradient magnetic fields (e.g., data defining the waveform of a gradient magnetic field pulse) is generated and stored in advance in association with time-point data, and this data is then read out in comparison with the time data that increases in real time, allowing a series of gradient magnetic fields to be generated in real time.

However, in the synchronization imaging using the external trigger, the preliminarily generated data for generating the gradient magnetic fields are unavailable after the time point at which the external trigger is inputted. Thus, if it is determined in the step ST305 that the external trigger is inputted, each gradient magnetic field corresponding to the time point after the input time point of the external trigger is deleted in the step ST306, and then, a series of gradient magnetic fields based on the pulse sequence are regenerated in association with the series of generated first time-point data in the step ST303.

In the step ST304, at the second time point (i.e., the transmitting time point of the next transmitting signal) after the generation time point of each of the series of gradient magnetic fields, the RF transmitting signal based on the pulse sequence is generated or regenerated in association with the second time-point data. Data for generating the RF transmitting signal (e.g., data defining the waveform of the RF pulse) is generated and stored in advance in association with time-point data, and this data is then read out in comparison with the time data that increases in real time, allowing the RF transmitting signal to be generated in real time, similarly to the series of gradient magnetic fields.

However, in the synchronization imaging using the external trigger, the preliminarily generated data for generating the RF transmitting signal are unavailable after the time point at which the external trigger is inputted. Thus, if it is determined in the step ST305 that the external trigger is inputted, each RF transmitting signal corresponding to the time point after the input time point of the external trigger is deleted in the step ST306, and then, the RF transmitting signal based on the pulse sequence is regenerated in the step ST304.

Figures 12A, 12B, 12C, 12D, 12E, 12F, 12G:
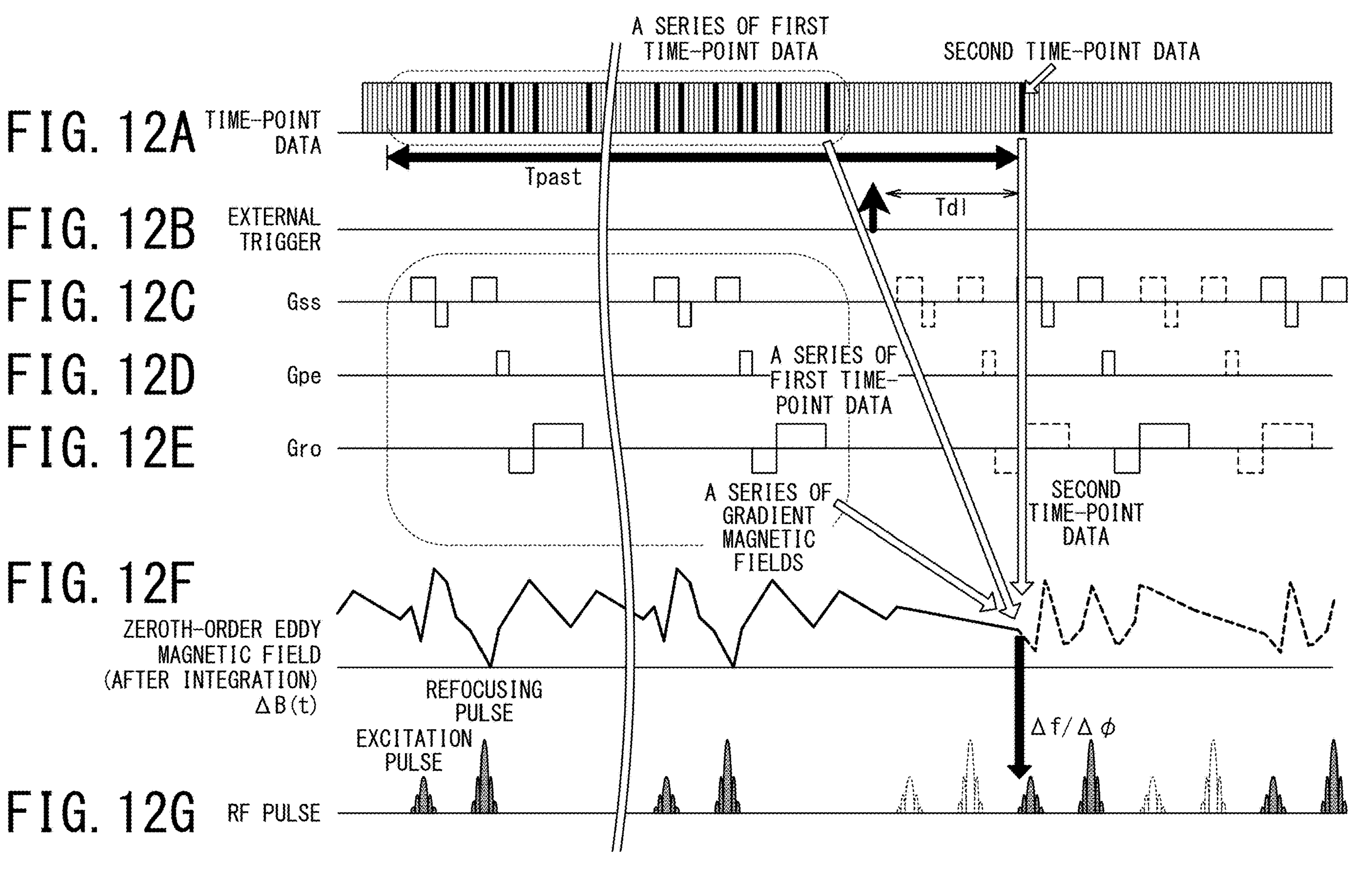
FIG. 12A to FIG. 12G are timing charts illustrating a concept of the transmitting processing when the external trigger is inputted.

FIG. 12A to FIG. 12G are timing charts illustrating a concept of the transmitting processing when the external trigger is inputted. FIG. 12B illustrates the input timing of the external trigger. In the case shown in FIG. 12A to FIG. 12G, the excitation pulse is generated and imaging is restarted at the second time point, which is after elapse of the delay time Tdl from the input time point of the external trigger. Thus, both the data for generating the RF transmitting signal and the data for generating the gradient magnetic fields corresponding to the period from the input time point of the external trigger to the second time point are deleted, as shown by the broken lines in FIG. 12C to FIG. 12E and FIG. 12G.

After elapse of the delay time Tdl from the input time point of the external trigger, a new RF pulse and a new series of gradient magnetic fields are generated as shown by the solid lines in FIG. 12C to FIG. 12E and FIG. 12G.

In the step ST105 of FIG. 11, the eddy magnetic fields at the second time point are estimated by using the series of gradient magnetic fields, the series of first time-point data, and the second time-point data. For the estimation of the eddy magnetic fields at the second time point which is the time of interest, the respective eddy magnetic fields based on the series of gradient magnetic fields actually applied in the past immediately before the second time are used, but not using the deleted gradient magnetic fields in the period between the external trigger input and the second time point. The decay amount of the eddy magnetic fields in accordance with the predetermined time constant is calculated by using respective time differences between the series of first time-point data, which are associated with the series of gradient magnetic fields actually applied in the past immediately before the second time point, and the second time-point data, which are data of the actual time of interest. Hence, even in the synchronization imaging using the external trigger, the eddy magnetic fields at the second time point (i.e., the generation time point of the excitation pulse after the input of the external trigger in the case of FIG. 12A to FIG. 12G) can be estimated with high accuracy.

The steps ST106 to ST108 in FIG. 11 are the same as those in FIG. 3, and duplicate descriptions are omitted.

Figure 13:
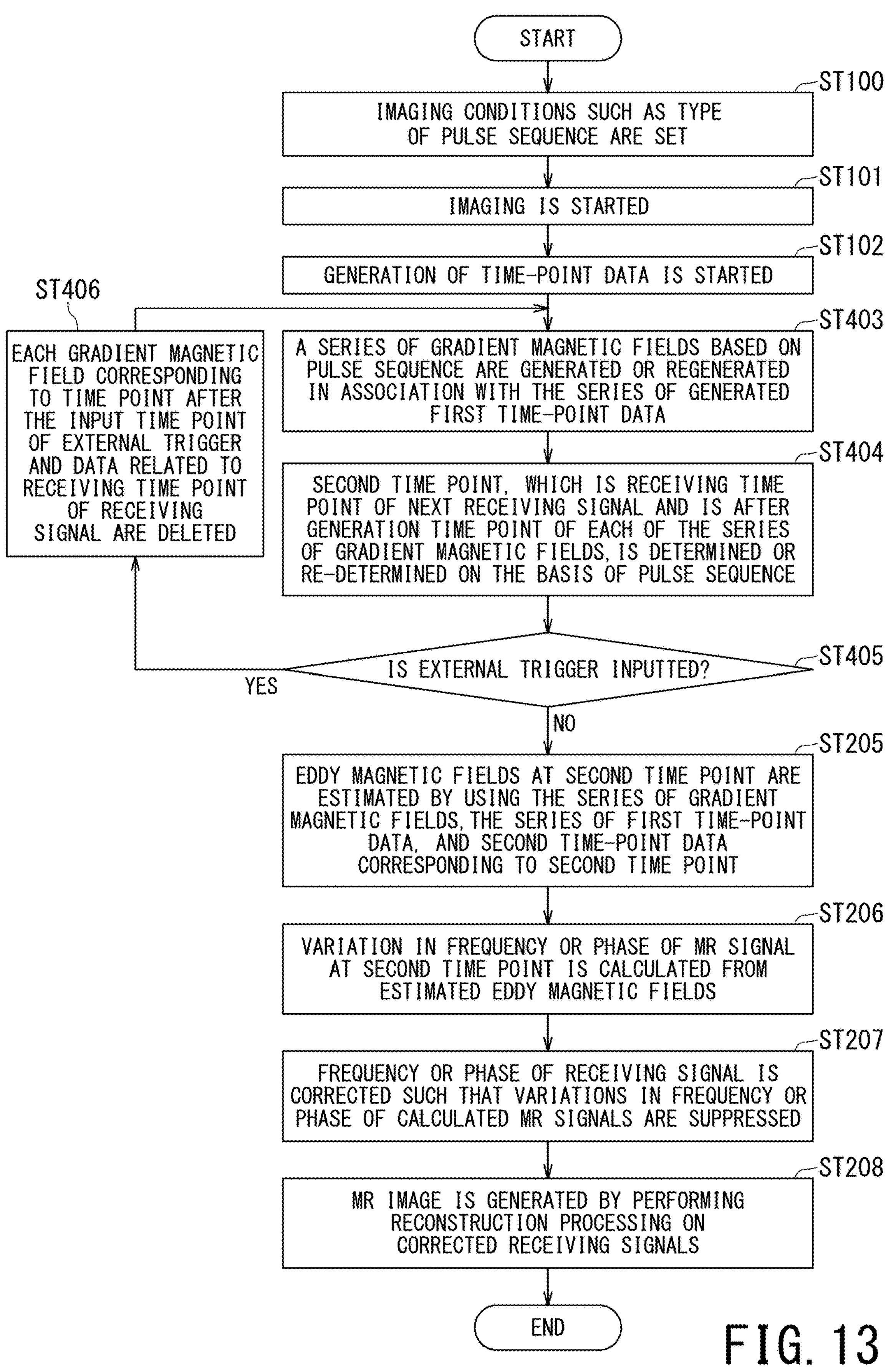
FIG. 13 is a flowchart illustrating the receiving processing when the external trigger is inputted.

FIG. 13 is a flowchart illustrating the receiving processing when the external trigger is inputted. The steps ST100 to ST102 in FIG. 13 is the same processing as the case where the external trigger is not inputted, and duplicate descriptions are omitted.

In the step ST403 of FIG. 13, a series of gradient magnetic fields based on the pulse sequence are generated or regenerated in association with the generated series of first time-point data. If it is determined in the step ST405 that the external trigger is inputted, each gradient magnetic field corresponding to the time point after the input time point of the external trigger is deleted in the step ST406 immediately before the step ST403, and then, a series of gradient magnetic fields based on the pulse sequence are regenerated in association with the series of generated first time-point data in the step ST403, similarly to the step ST303 of FIG. 11.

In the step ST404, the second time point, which is the receiving time point of the next receiving signal and is after the generation time point of each of the series of gradient magnetic fields, is determined or re-determined on the basis of the pulse sequence. If the external trigger is inputted, the receiving time point after input of the external trigger is determined according to the input timing of the external trigger, and thus, in the step ST404, the second time point, which is the receiving time point of the next received signal, is "redetermined" on the basis of the pulse sequence.

FIG. 14A to FIG. 14G are timing charts illustrating a concept of the receiving processing when the external trigger is inputted. In the case shown in FIG. 14A to FIG. 14G, similarly to FIG. 12A to FIG. 12G, the excitation pulse is generated and imaging is restarted after elapse of the delay time Tdl from the input time point of the external trigger. Further, the receiving period (i.e., sampling period) of the MR signal starts at the time of interest (i.e., at the second time point) which is after elapse of the predetermined echo time TE from the application timing of the excitation pulse.

The processing circuitry 340 deletes the data for generating the RF transmitting signal, the data for generating the gradient magnetic fields corresponding to the period from the input timing of the external trigger until the end of the delay time Tdl as shown by the broken line in FIG. 14C to FIG. 14E, and also the data regarding the receiving time point corresponding to this period.

In the step ST205, the eddy magnetic fields at the second time point are estimated by using the series of gradient magnetic fields, the series of first time-point data, and the second time-point data corresponding to the second time point. The second time point, which is the time of interest, is the actual time of interest newly determined after application of the external trigger. In addition, the gradient magnetic fields to be used for estimating the eddy magnetic fields are each of the series of gradient magnetic fields that are actually applied in the past immediately before the second time point.

Hence, even in the synchronization imaging using the external trigger, the eddy magnetic fields at the second time point (i.e., the sampling time-point of the receiving signal after the input of the external trigger in the case of FIG. 14A to FIG. 14G) can be estimated with high accuracy.

According to the MRI apparatus of each of the above-described embodiments, even in an imaging method in which imaging is performed in synchronization with an external trigger signal, the eddy magnetic fields can be estimated with high accuracy and deterioration in image quality caused by the eddy magnetic fields can be sufficiently suppressed.

While certain embodiments have been described, these embodiments have been presented by way of example only, and are not intended to limit the scope of the invention. Indeed, the novel methods and systems described herein may be embodied in a variety of other forms; furthermore, various omissions, substitutions and changes in the form of the methods and systems described herein may be made without departing from the spirit of the invention. The accompanying claims and their equivalents are intended to cover such forms or modifications as would fall within the scope and spirit of the invention.

What is claimed is:

1. An MRI apparatus comprising processing circuitry configured to:

continuously generate time-point data in increments of a predetermined time length;

generate a series of gradient magnetic fields based on a predetermined pulse sequence in association with a series of first time-point data that are the generated time-point data and correspond to respective generation time points of the series of gradient magnetic fields;

acquire an external trigger in association with trigger-time-point data that are the generated time-point data and correspond to an acquisition time point of the external trigger;

estimate a value of an eddy magnetic field at a second time point by using the series of gradient magnetic fields and respective time differences between the series of first time-point data and second time-point data, wherein the respective time differences change depending on when the external trigger is acquired, the second time point being after the respective generation time points of the series of gradient magnetic fields, and the eddy magnetic field being resulting from the series of gradient magnetic fields;

calculate a frequency variation or phase variation of an MR signal caused by the eddy magnetic field at the second time point from the estimated value of the eddy magnetic fields; and correct a frequency or phase of at least one of an RF transmitting signal to be applied to an object and the MR signal emitted from the object, by using the calculated frequency variation or the phase variation.

2. The MRI apparatus according to claim 1, wherein:

each of the eddy magnetic fields resulting from the series of gradient magnetic fields is a zeroth-order eddy magnetic field that decays exponentially with a predetermined time constant; and the processing circuitry is configured to estimate the value of the eddy magnetic field at the second time point by integrating each of the zeroth-order eddy magnetic fields that are estimated by using the respective time differences at the second time point.

3. The MRI apparatus according to claim 1, wherein the processing circuitry is configured to further generate the RF transmitting signal based on the predetermined pulse sequence in association with the second time-point data.

4. The MRI apparatus according to claim 3, wherein the processing circuitry is configured to:

estimate the value of the eddy magnetic field at a transmitting time point of the RF transmitting signal by using the respective time differences between the series of first time-point data and the second time-point data corresponding to the generation time point of the RF transmitting signal; and generate the RF transmitting signal by using the estimated value of the eddy magnetic field to correct a frequency or phase of the RF transmitting signal in such a manner that a variation in frequency or phase of the MR signal caused by the eddy magnetic field is suppressed.

5. The MRI apparatus according to claim 4, wherein the processing circuitry is configured to generate the RF transmitting signal by using the estimated value of the eddy magnetic field to correct the frequency or phase of the RF transmitting signal at each time point that advances in predetermined increments during a transmitting period of the RF transmitting signal in such a manner that the variation in frequency or phase of the MR signal caused by the eddy magnetic field is suppressed.

6. The MRI apparatus according to claim 4, wherein the processing circuitry is configured to generate the RF transmitting signal as a pulse including at least one of an excitation pulse, an inversion pulse, a refocusing pulse and a labeling pulse.

7. The MRI apparatus according to claim 4, wherein the processing circuitry is configured to generate the RF transmitting signal as a pulse including at least one of a fat suppression pulse and a water excitation pulse.

8. The MRI apparatus according to claim 1, wherein the processing circuitry is configured to sample and receive the MR signal in association with the second time-point data depending on the predetermined pulse sequence.

9. The MRI apparatus according to claim 8, wherein the processing circuitry is configured to:

estimate the value of the eddy magnetic field at a receiving time point of the MR signal by using respective time differences between the series of first time-point data and the second time-point data corresponding to the receiving time point of the MR signal; and convert a frequency of the MR signal into a baseband or correct a frequency or phase of the MR signal having been converted into the baseband in such a manner that a variation in frequency or phase of the MR signal caused by the eddy magnetic field is suppressed, by using the estimated value of the eddy magnetic fields.

10. The MRI apparatus according to claim 9, wherein the processing circuitry is configured to correct a local frequency for converting the frequency of the MR signal into the baseband in an analog domain or digital domain in such a manner that the variation in frequency or phase of the MR signal caused by the eddy magnetic field is suppressed.

11. The MRI apparatus according to claim 9, wherein the processing circuitry is configured to correct a frequency or phase of the MR signal having been converted into the baseband by digital calculation in such a manner that the variation in frequency or phase of the MR signal caused by the eddy magnetic field is suppressed.

* * * * *